US012411128B2

(12) United States Patent
Khine et al.

(10) Patent No.: US 12,411,128 B2
(45) Date of Patent: Sep. 9, 2025

(54) METHODS AND APPARATUSES FOR PREDICTION OF MECHANISM OF ACTIVITY OF COMPOUNDS

(71) Applicants: The Regents of the University of California, Oakland, CA (US); Novoheart International Limited, Hong Kong (CN)

(72) Inventors: Michelle Khine, Irvine, CA (US); Eugene Lee, Irvine, CA (US); Tang Wai Ronald Adolphus Li, Pok Fu Lam (HK); David Dan Tran, Aliso Viejo, CA (US)

(73) Assignees: The Regents of the University of California, Oakland, CA (US); Novoheart International Limited, Hong Kong (CN)

( * ) Notice: Subject to any disclaimer, the term of this patent is extended or adjusted under 35 U.S.C. 154(b) by 1585 days.

(21) Appl. No.: 16/019,332

(22) Filed: Jun. 26, 2018

(65) Prior Publication Data
US 2018/0372724 A1    Dec. 27, 2018

Related U.S. Application Data

(60) Provisional application No. 62/525,044, filed on Jun. 26, 2017.

(51) Int. Cl.
*G01N 33/50* (2006.01)
*G01N 30/86* (2006.01)
(Continued)

(52) U.S. Cl.
CPC ..... *G01N 33/5061* (2013.01); *G01N 30/8675* (2013.01); *G01N 33/4836* (2013.01);
(Continued)

(58) Field of Classification Search
CPC .......... G01N 33/5061; G01N 30/8675; G01N 33/4836; G01N 33/48707;
(Continued)

(56) References Cited

U.S. PATENT DOCUMENTS 9,612,234 B2 * 4/2017 Li .................... G01N 33/48728
11,913,940 B2 * 2/2024 Miklas .................. C12M 23/12
(Continued)

OTHER PUBLICATIONS

Turnbull et al. Fed. Am. Soc. Exp. Biol. 28, 644-654, 2014.*
(Continued)

*Primary Examiner* — Jesse P Frumkin
(74) *Attorney, Agent, or Firm* — Knobbe, Martens, Olson & Bear, LLP

(57) ABSTRACT

A platform configured to predict type or family of an unknown drug candidate compound, the platform including: a living cell or a tissue; a detector that measures an indicator of a cellular response by the living cell or tissue upon exposure to the unknown drug candidate compound; a memory configured to store data related to the indicator of the cellular response detected by the detector from a library of drug types and/or families; and one or more processing unit(s) configured to: process the data related to the indicator of the cellular response of the living cell or tissue upon exposure to the unknown drug candidate compound, and compare cellular response data from the library of drug types and/or families, so that a drug type and/or a drug family and/or a mechanism of action of the unknown drug candidate compound can be predicted on the basis of a similarity between the detected cellular response data of the unknown drug candidate compound and the cellular response data of the library of drug types and/or families. Also disclosed are methods of screening an unknown drug, including: comparing the data measured from a test cell to corresponding cellular response data in a library of known
(Continued)

drug types, and determining a relationship between the unknown drug and a known drug type or a known drug family to predict the type or family of the unknown drug.

19 Claims, 10 Drawing Sheets

(51) Int. Cl.
*G01N 33/483* (2006.01)
*G01N 33/487* (2006.01)
*G16B 20/00* (2019.01)
*G16B 40/00* (2019.01)
*G16B 40/20* (2019.01)
*G16C 20/00* (2019.01)
*G16C 20/20* (2019.01)
*G16C 20/30* (2019.01)
*G16C 20/40* (2019.01)
*G16C 20/64* (2019.01)
*G16C 20/70* (2019.01)
*G16H 40/00* (2018.01)
*G16H 50/00* (2018.01)

(52) U.S. Cl.
CPC . *G01N 33/48707* (2013.01); *G01N 33/48728* (2013.01); *G01N 33/48785* (2013.01); *G01N 33/48792* (2013.01); *G01N 33/5088* (2013.01); *G16B 20/00* (2019.02); *G16B 40/00* (2019.02); *G16B 40/20* (2019.02); *G16C 20/00* (2019.02); *G16C 20/20* (2019.02); *G16C 20/30* (2019.02); *G16C 20/40* (2019.02); *G16C 20/64* (2019.02); *G16C 20/70* (2019.02); *G16H 40/00* (2018.01); *G16H 50/00* (2018.01)

(58) Field of Classification Search
CPC ....... G01N 33/48728; G01N 33/48785; G01N 33/5088; G01N 33/48792; G16B 20/00; G16B 40/00; G16B 40/20; G16C 20/00; G16C 20/20; G16C 20/30; G16C 20/40; G16C 20/64; G16C 20/70; G16H 40/00; G16H 50/00
See application file for complete search history.

(56) References Cited

U.S. PATENT DOCUMENTS

| | | | | |
|---|---|---|---|---|
| 2003/0064358 | A1* | 4/2003 | Elson | G01N 3/38 435/325 |
| 2007/0042347 | A1* | 2/2007 | Rosen | G01N 33/6872 435/4 |
| 2009/0227469 | A1* | 9/2009 | Conklin | C12N 5/0657 506/10 |
| 2011/0300569 | A1* | 12/2011 | Li | G01N 33/4836 435/29 |
| 2012/0094323 | A1* | 4/2012 | Dekker | G01N 1/30 216/17 |
| 2012/0231482 | A1* | 9/2012 | Murray | G01N 33/6887 435/7.1 |
| 2014/0349332 | A1* | 11/2014 | Yasuda | B01L 3/5085 435/29 |
| 2015/0253307 | A1* | 9/2015 | Parker | G01N 33/5082 506/10 |
| 2018/0356400 | A1* | 12/2018 | Degot | G01N 33/5088 |
| 2024/0133873 | A1* | 4/2024 | Miklas | C12M 23/16 |

OTHER PUBLICATIONS

Lee et al. Scientific Reports, 5:11817, 1-12, 2015.*
Machine learning. (2003). In B. Pfaffenberger, Webster's New World Computer Dictionary (10th ed.). Houghton Mifflin Harcourt. https://search.credoreference.com/articles/Qm9va0FydGljbGU6MTU2NjE3Ng==? aid=279753 (Year: 2003).*

* cited by examiner

METHODS AND APPARATUSES FOR PREDICTION OF MECHANISM OF ACTIVITY OF COMPOUNDS

BACKGROUND OF THE INVENTION

Field of the Invention

This application is directed to pharmacological screening technologies including methods and apparatuses for in vitro screening of potential drug compounds.

Description of the Related Art

While drug screening platforms may vary in their acquisition methodology (e.g., $Ca^{2+}$ transients, field potential duration, or force measurements), the readouts of systems are predominantly composed of an array of parameters that describe the behavior or shape of individual contractile events. Combining this with the number of experimental conditions (e.g., drug concentrations) can yield high-dimensional datasets that make it difficult to draw definitive conclusions. In addition, as these platforms are meant for high-throughput screens, the analysis of the datasets needs to be automated. Such requirements indicate that traditional methods of pre-selecting one or a few parameters for statistical analysis may not be adequate. By selectively examining a few parameters independently of one another, there is a risk of not detecting information that differentiates the behavior of control (either normal or diseased) cardiomyocytes (CMs) or their tissues from those exposed to cardioactive compounds.

While the concept of examining and integrating multiple parameters from waveforms has been pursued lately, some studies have suggested that only a few parameters (e.g., peak count) are necessary in assessing a compound's cardioactivity as other parameters are derivatives of the select few and provide no further mechanistic insight (Sirenko, O. et al. 2013 *J Biomol Screen* 18: 39-53; Peters, M. F. et al. 2012 *Assay Drug Dev Technol* 10(6): 525-432; Lu, H. R. et al. 2015 *Toxicol Sci* 148: 503-516; Pointon, A. et al. 2017 *Toxicol Sci* 155(2): 444-457; Pointon, A. et al. 2015 *Toxicol Sci* 144(2): 227-237; Reif, D, M. et al. 2013 *Bioinformatics* 29(3): 402-403; Clements, M. et al. 2015 *Toxicol Sci* 148(1): 241-260). However, this applies only under certain specific but not all conditions.

Withdrawal of drugs in late stage development, and even those with market approval, most often occurs due to previously undetected drug-induced cardiotoxicity. Unpredicted drug-induced cardiotoxicity jeopardizes patients' lives, erodes public trust in the regulatory process, and financially burdens the pharmaceutical industry. For example, cisapride, a gastrointestinal drug intended to treat heart burn, was reported to have caused serious ventricular arrhythmias and sudden deaths prior to withdrawal (Ferriman, 2000). The associated pharmaceutical company agreed to settle lawsuits for a total of $90 million U.S. dollars for 300 deaths and 16,000 injuries (Harris and Koli, 2005). Some limited progress has been made to facilitate better safety through the adoption of FDA guidelines that recommend screening new drugs with the human Ether-à-go-go-Related Gene (hERG) inhibition assay (FDA, 2005). Nonetheless, within the past decade, an assortment of market approved therapeutics (e.g., clobutinol, sibutramine, and tegaserod) had to be withdrawn due to unpredicted drug-induced cardiotoxicity (Li et al., 2016; US Food and Drug Administration, 2007).

The need for more accurate and faster pre-clinical detection methods has led to the emergence of a variety of screening platforms in recent years. A majority of these detection systems have begun to utilize human pluripotent stem cell-derived cardiomyocytes (hPSC-CMs). These cells are more physiologically similar to human myocardium than laboratory animals or genetically transformed non-cardiac cell lines (e.g. human embryonic kidney cells) (Dick et al., 2010). Aside from the commonality of using hPSC-CMs, these platforms greatly vary in their setup, including differences in tissue geometry. Certain platforms employ hPSC-CMs or other sources CMs in a two-dimensional manner (e.g., monolayer), while others attempt to recapitulate aspects of the three dimensional environment of native myocardium by modeling the cells as cardiac muscle fibers or heart chambers (Chen et al., 2014; Huebsch et al., 2016; Luna et al., 2011; Shum et al., 2017; Turnbull et al., 2014; Wang et al., 2013). These systems can also drastically differ in their methodology of quantifying changes in hPSC-CMs exposed to cardioactive compounds. Some systems examine the electrophysiological properties while others focus on the calcium transients or measurements of contractility (e.g., shortening, force, pressure) generated by the cardiomyocytes (Lu et al., 2015; Maddah et al., 2015; Navarrete et al., 2013; Zhang et al., 2014).

SUMMARY OF THE INVENTION

While the experimental platforms may vary, quantitative readouts generally characterize individual contractile events. Combining this with the number of experimental conditions (e.g., various pacing frequencies or drug concentrations) can yield high-dimensional datasets that make it difficult to draw definitive conclusions. Researchers often simplify the raw data by preselecting a limited number of parameters as an attempt to comprehend the complexity of the data, albeit losing information in the process. Without full interpretation of such a rich dataset, there is risk of not detecting information that differentiates the behavior of control CMs from those exposed to cardioactive compounds. In addition, as these platforms are meant for high-content screens, the analysis of the datasets needs to be automated.

Rather, holistic approaches must be developed to optimize the utility of datasets generated from screening platforms. Machine learning has been shown to handle such high dimensional datasets in an automated fashion (Lee et al., 2015). We previously demonstrated that Support Vector Machine (SVM), a supervised learning algorithm, can be used to consolidate 12 parameters, which characterized contractile behavior of hPSC-CMs exposed to cardioactive compounds, into a singular quantitative index that expressed the level of induced cardioactivity (Lee et al., 2015). Machine learning can be further leveraged into a suite of tools that provide more in-depth details of hPSC-CM behavior when exposed to cardioactive compounds.

Some embodiments relate to a platform configured to predict type or family of an unknown drug candidate compound, the platform comprising:
   (a) a living cell or a tissue;
   (b) a detector that measures an indicator of a cellular response by the living cell or tissue upon exposure to the unknown drug candidate compound;
   (c) a memory configured to store data related to the indicator of the cellular response detected by the detector from a library of drug types and/or families; and (d) one or more processing unit(s) configured to:
  (i) process the data related to the indicator of the cellular response of the living cell or tissue upon exposure to the unknown drug candidate compound, and
  (ii) compare cellular response data from the library of drug types and/or families, so that a drug type and/or a drug family and/or a mechanism of action of the unknown drug candidate compound can be predicted on the basis of a similarity between the detected cellular response data of the unknown drug candidate compound and the cellular response data of the library of drug types and/or families.

In some embodiments, the living cell or tissue is a model of cardiac muscle fiber.

In some embodiments, the living cell or tissue is configured as a human cardiac tissue strip (hCTS).

In some embodiments, the platform is configured to electrically pace the living cell or tissue and wherein the cellular response data is captured at a variety of pacing frequencies.

In some embodiments, the processing unit is configured to implement machine learning.

In some embodiments, the machine learning utilizes predetermined parameters of cellular response data to classify the cellular response data measured in response to the unknown drug and the cellular response data from the library of drug types and/or families.

In some embodiments, the predetermined parameters of the cellular response data comprise force data, the force data comprising one or more of the following parameters:
  (a) pacing frequency;
  (b) a captured pacing frequency;
  (c) a maximum force generated (amplitude);
  (d) a duration of rise from a cutoff level to maximum force in a contraction phase;
  (e) a duration of decline from maximum force to a cutoff level in a relaxation phase;
  (f) an area under the curve of rise from a cutoff level to maximum force;
  (g) an area under the curve of decline from maximum force to a cutoff level;
  (h) a maximum change of force over time ($\Delta F/\Delta t$) of contraction phase; and
  (i) a maximum change of force over time ($\Delta F/\Delta t$) of relaxation phase.

In some embodiments the predetermined parameters of the cellular response data comprise force data, the force data comprising one or more of the following parameters:
  desired pacing frequency,
  captured pacing frequency,
  max force generated (amplitude),
  duration of rise from 95% cutoff to max force (contraction phase),
  duration of decline from max force to 95% cutoff (relaxation phase),
  area under the curve of rise from 95% cutoff to max force,
  area under the curve of decline from max force to 95% cutoff,
  max change of force over time ($\Delta F/\Delta t$) of contraction phase,
  max change of force over time ($\Delta F/\Delta t$) of relaxation phase,
  duration of rise from 50% cutoff to max force,
  duration of decline from max force to 50% cutoff,
  area under the curve of rise from 50% cutoff to max force,
  area under the curve of decline from max force to 50% cutoff,
  duration of rise from 25% cutoff to max force,
  duration of decline from max force to 25% cutoff to max force,
  area under the curve of rise from 50% cutoff to max force, and
  area under the curve of decline from max force to 50% cutoff.

In some embodiments, the cellular response data comprises a measure of cell or tissue motion and/or electrical conduction and/or calcium flux and the detector is capable of detecting motion and/or electrical conduction and/or calcium flux in the living cell or tissue following exposure to the drug.

In some embodiments, the electrical conduction detected corresponds to one or more of a micro-impedance signal and an electrophysiological signal.

In some embodiments, the processing unit is configured to output dosing information of the unknown drug candidate compound based upon a comparison to the cellular response data of one or more members of the library.

In some embodiments, the platform comprising a library of drug types and/or families stored in the memory.

In some embodiments, each drug type or drug family is characterized by a plurality of distinct compounds within the drug type or drug family.

Some embodiments relate to a method of screening an unknown drug, comprising:
  (a) exposing a test cell or a tissue to the unknown drug,
  (b) quantifying a cellular response by obtaining cellular response data measured from the test cell in response to the unknown drug,
  (c) comparing the data measured from the test cell to corresponding cellular response data in a library of known drug types,
  (d) determining a relationship between the unknown drug and a known drug type or a known drug family to predict the type or family of the unknown drug.

In some embodiments, the cellular response data is indicative of cardioactivity.

In some embodiments, the test cell or tissue is a human cardiac tissue construct In some embodiments, a degree to which a compound is cardiotoxic/cardioactive is predicted.

In some embodiments, a mechanism of cardioactivity or cardiotoxicity of a compound is predicted.

In some embodiments, machine learning is used to form the library of cellular response data of known drug types.

In some embodiments, the method comprises comparing the cellular response data of the test cell to a library of corresponding cellular response data of known drug types is done by a series of binary classifications.

In some embodiments, the method comprises calculating a singular quantitative index generated by a supervised learning algorithm to consolidate a plurality of parameters of a cellular response into a singular quantitative index.

In some embodiments, the supervised learning algorithm is a binary support vector machine (SVM) approach.

In some embodiments, differences in drug response between patient-specific heart cells of different genetic backgrounds are compared.

In some embodiments, the library of cellular response data of known drug types contains data from patients with known cardiac diseases.

Embodiments disclosed herein provide improvements of pharmacological screening technology. In some embodiments, a platform that employs cardiac tissue constructs and machine learning is configured to provide relevant information for evidence-based decision-making in drug development. In some embodiments, the cardiac tissue is a human cardiac tissue strip (hCTS). Some embodiments utilize human ventricular cardiac tissue strips (hvCTS). Some embodiments utilize human atrial cardiac tissue strips (haCTS). Methods disclosed herein can 1) determine if and to what degree a compound is cardiotoxic/cardioactive, 2) predict a mechanism of cardioactivity or cardiotoxicity of a compound, and/or 3) report a drug response, potency and other relationships between compounds among other benefits.

Embodiments herein provide biomedical engineering improvements, including advancements in the study of effects of physical and chemical stimulants on hvCTS or haCTS, for example, which are models of cardiac muscle fiber.

Embodiments herein provide improvements of software for analysis of cardiac cells. A holistic approach in analyzing high dimensional data of cardiac functional data and readouts thereof with machine learning is used. Various approaches summarize and provide simple metrics. Various approaches integrate data or parameters across platforms.

The platforms described here are able to report cardioactivity-related information of a compound through drug screens of hCTS, which are able to model cardiac muscle fibers. hCTS are human cardiac tissue strips that may be ventricular, atrial or other cell composition, such as including various support cells or therapeutic cells or agents. Some investigators use rodent or other animal-derived cardiomyocytes Skeletal muscle tissue strips (e.g., smooth muscle strips) can also be characterized using this technology Machine learning may be used to determine whether a compound is cardioactive and to what degree (e.g., with a singular quantitative index/metric), predict a compound's cardioactive mechanism(s) based on a drug library, and/or provide drug response relationships between compounds. Machine learning can be employed in a holistic approach that can analyze and consolidate multiple parameters derived from one or a plurality of sources of data (e.g., from one or more readouts, such as a force waveform or an electrical signal). Previous studies have assumed that only a few parameters are necessary for such analyses when cardiomyocytes are spontaneously beating. However in some approaches of using the hCTS platforms, the tissue strips are paced at a plurality of (e.g., four) different pacing frequencies, which decouples the force-frequency relationship and provides additional insights on how compounds can affect measured activity curves. Information output by the platform aids in the streamlining of drug development through evidence-based decisions.

It should be noted that this analysis can be applied to platforms with various tissue geometries (e.g., monolayer or 3D tissue constructs) and monitoring methodologies. Furthermore, the overall analysis can be greatly benefited by integrating data across these platforms.

The embodiments disclosed herein, which permit analysis and consolidation of multiple parameters derived from one or a plurality of sources of data provide a number of advantages over selectively examining a few parameters independently of one another. The platforms can look at multiple parameters derived from the force tracing and/or electrical signal tracing of each or of a plurality of cellular responses, e.g., contractile event(s). These parameters describe the overall shape of the traces. Machine learning is an example of a technique that is able to automatically distinguish, e.g., by determining advantageous or optimal planes that separate, the data points of control cardiomyocytes from those exposed to cardioactive drugs. Thus, the larger number of parameters (compared to the select few in traditional analysis) can potentially lead to better detection of cardioactivity (higher sensitivity and specificity). The machine learning technique is suited to handle high dimensional data sets.

This method disclosed here is more efficient than traditional methods. For example, if a platform has 10 parameters of interest, traditional methods need to examine at least 1023 possible combinatorial forms of the parameters. Pairwise comparisons of 10 parameters results in $2^{10}$, which is 1023 combinations, but the number is much greater if one considers multiple combinations of parameters. With the described machine learning approach, all the data is examined simultaneously.

The pacing of the tissue strips allows for the examination of a compound's effect on the force-frequency curve.

Another advantage is that one or more drug classification library can be established without any guidelines, rubrics, or thresholds. Thus, when a new drug class is to be entered into a database or a library of drug types and/or families, no human or manual edits need to be made. Rather it can be done in an efficient and automated manner.

The prediction of a compound's mechanism of cardioactivity can be based on in vitro data, not in silico data. The software is flexible and can be adapted to multiple types of readouts.

hCTS provide a direct way to measure changes in force outputs and/or electrical conduction of cardiac tissues when exposed to cardioactive drugs.

DETAILED DESCRIPTION OF THE PREFERRED EMBODIMENT

Figure 1:
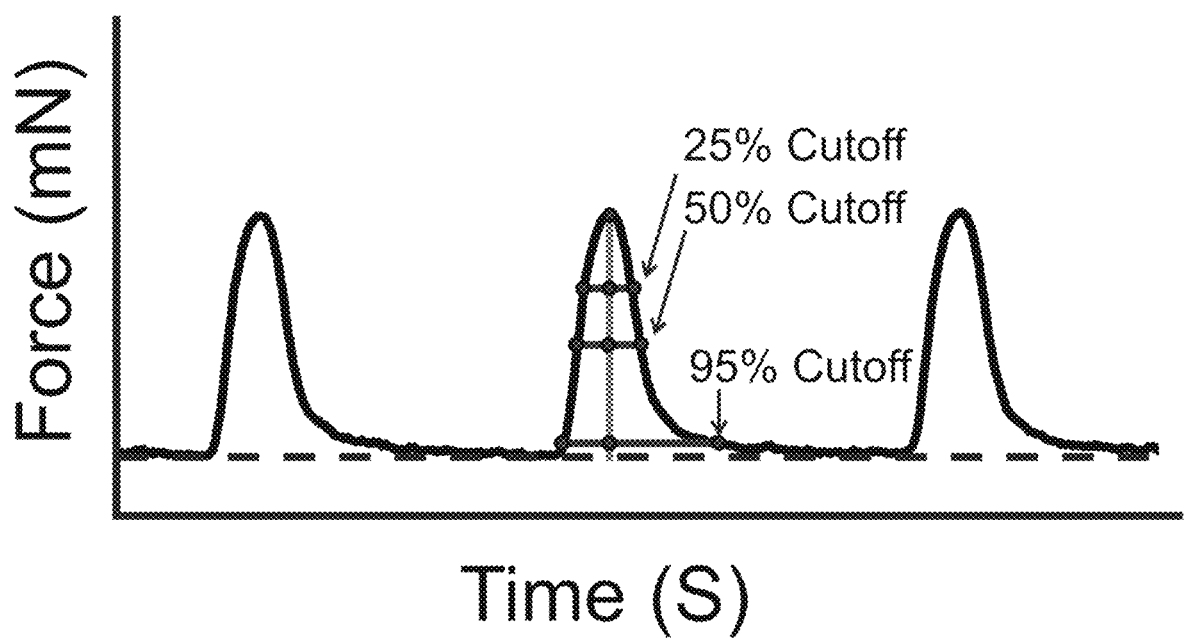
FIG. 1 is a plot of force generated by the hvCTS and further illustrates three cutoff points (at 25, 50, and 95% of the max force generated) which can be calculated or used to summarize changes to the overall shape of the force waveform. A vertical line indicates the time at which max force is generated.

We hypothesize that multi-classification algorithms can be implemented to create a model to define drug classes and subsequently predict an unknown compound's mechanistic action. Such information would assist in streamlining the drug discovery pipeline, allowing for the rapid identification of select compounds for more in-depth follow up assays. In addition, this information coupled with knowledge of a predicted class can guide scientists to efficiently and selectively screen for specific drug-to-drug interactions that prompt cardiotoxicity (e.g., disruption of $Ca^{2+}$ handling when sofosbuvir and amiodarone are combined) instead of relying on the traditional brute force approach (Millard et al., 2016). Furthermore, drug response relationships between the unknown compound and the library can be determined.

We examined a database containing drug screens of various compounds on twitch force measurements from human ventricular cardiac tissue strips (hvCTS) engineered from hPSC-CMs embedded in a 3D collagen-based matrix (Turnbull et al., 2014). A unique aspect of these screens was that the hvCTSs were electrically paced at four different frequencies from 0.5 to 2.0 Hz, spanning a physiologic range. These measurements interrogated the influence of cardioactive compounds on the hvCTS force-frequency relationship, and contributed to a high dimensional dataset. We selected a total of twelve compounds with acute cardiac effects that represented five drug classes (1. $Ca^{2+}$ channel blockers, 2. adrenergic agonists, 3. cardiac glycosides, 4. hERG $K^+$ channel blockers, and 5. angiotensin converting enzyme (ACE) inhibitors) along with one reference compound (aspirin). We report for the first time the use of machine learning to establish a drug classification model based on hvCTS contractile behavior (using half of the selected compounds) and subsequently demonstrate predictive capabilities by having the model classify unknown compounds, which were withheld from the machine during training.

Accurately predicting cardioactive effects of new molecular entities for therapeutics remains a daunting challenge. Immense research effort has been focused towards creating new screening platforms that utilize human pluripotent stem cell (hPSC)-derived cardiomyocytes and three-dimensional engineered cardiac tissue constructs to better recapitulate human heart function and drug responses. As these new platforms become increasingly sophisticated and high-throughput, the drug screens result in larger, higher-dimensional datasets. New automated analysis methods must therefore be developed in parallel to fully comprehend the cellular response across a multidimensional parameter space. Here, we describe the use of machine learning to comprehensively analyze, in one embodiment, 17 functional parameters derived from force readouts of hPSC-derived ventricular cardiac tissue strips (hvCTS) electrically paced at a range of frequencies and exposed to a library of compounds. A generated metric is effective for then determining the cardioactivity of a given drug. Furthermore, we demonstrate a classification model that can automatically predict the mechanistic action of an unknown cardioactive drug.

Formation of Drug Classification Model

To form the drug classification model, the screens of twelve compounds (Table 1) acquired on the hvCTS platform were used.

TABLE 1

Library Compounds

| Compound Name | Class | Description | Test Range (M) |
|---|---|---|---|
| Nifedipine | $Ca^{2+}$ Channel Blocker | A L-type $Ca^{2+}$ channel blocker known to shorten action potential duration (Harris et al., 2013). | $10^{-8}$ to $3.0 \times 10^{-5}$ |
| Mibefradil | $Ca^{2+}$ Channel Blocker | A tetralol derivative that blocks both L- and T-type $Ca^{2+}$ channels with higher affinity for T-type (Martin et al., 2000). | $10^{-9}$ to $3.0 \times 10^{-6}$ |
| Isoproterenol | Adrenergic Agonist | A mixed beta-adrenergic agonists. Compound is nonselective in terms of beta receptors (Steinberg, 1999). | $10^{-8}$ to $10^{-4}$ |
| Norepinephrine | Adrenergic Agonist | Mixed adrenergic agonist that stimulates both alpha- and beta-receptors (Yang et al., 2014) | $10^{-9}$ to $10^{-5}$ |
| Digoxin | Cardiac Glycoside | A cardiac glycoside that inhibits that $Na^+/K^+$-ATPase, resulting in higher intracellular $Na^+$. Higher $Na^+$ concentration suppresses the $Na^+/Ca^{2+}$ exchanger and causing the accumulation of intracellular $Ca^{2+}$ (Katz et al., 2010). | $10^{-8}$ to $10^{-4}$ |
| Ouabain | Cardiac Glycoside | A cardiac glycoside that affects $Na^+/K^+$-ATPase, which consists of both alpha and beta-subunits. Has a lower affinity for alpha subunits than digoxin (Katz et al., 2010). | $10^{-8}$ to $10^{-4}$ |
| Flecainide | hERG $K^+$ Channel Blocker | A mixed hERG $K^+$ blocker that also inhibits $Na^+$ channels, causing effects on action potential's repolarization and conduction (Harris et al., 2013). | $10^{-8}$ to $10^{-4}$ |

TABLE 1-continued

Library Compounds

| Compound Name | Class | Description | Test Range (M) |
|---|---|---|---|
| E-4031 | hERG K⁺ Channel Blocker | A pure hERG K⁺ channel blocker known for pro-arrhythmic potential (Ziupa et al., 2014). | $10^{-8}$ to $10^{-4}$ |
| Cisapride | hERG K⁺ Channel Blocker | A serotonin (5-HT$_4$) receptor agonists that also inhibits the hERG K⁺ channel (Wong et al., 2010). | $10^{-8}$ to $10^{-4}$ |
| Lisinopril | ACE Inhibitor | An ACE inhibitor, which reduces vasoconstriction and lowers blood pressure in patients (Williams, 1988). | $10^{-8}$ to $10^{-4}$ |
| Ramipril | ACE Inhibitor | An ACE inhibitor. It does not block ACE until it is converted by liver (Williams, 1988). | $10^{-9}$ to $10^{-5}$ |
| Aspirin | Non-cardioactive Reference | Nonsteroidal ant-inflammatory drug that has been shown to have no cardioactive effects in screening platforms (Maddah et al., 2015). | $10^{-8}$ to $10^{-4}$ | hERG—Human ether-a-go-go-related gene
ACE—Angiotensin-converting-enzyme

Each of the compounds, with the exception of aspirin, belonged to one of five classes with each class comprising a minimum of two compounds. Aspirin functioned as a reference for a cardiac-neutral compound. To quantify the cardioactive effects of these compounds, 17 parameters were derived from each contractile event recorded in the hvCTS twitch force vs. time tracings (FIG. 1). The parameters include:

1. Desired pacing frequency.
2. Captured pacing frequency.
3. Max force generated (amplitude).
4. Duration of rise from 95% cutoff to max force (contraction phase).
5. Duration of decline from max force to 95% cutoff (relaxation phase).
6. Area under the curve of rise from 95% cutoff to max force.
7. Area under the curve of decline from max force to 95% cutoff.
8. Max change of force over time ($\Delta F/\Delta t$) of contraction phase.
9. Max change of force over time ($\Delta F/\Delta t$) of relaxation phase.
10. Duration of rise from 50% cutoff to max force.
11. Duration of decline from max force to 50% cutoff.
12. Area under the curve of rise from 50% cutoff to max force.
13. Area under the curve of decline from max force to 50% cutoff.
14. Duration of rise from 25% cutoff to max force.
15. Duration of decline from max force to 25% cutoff to max force.
16. Area under the curve of rise from 50% cutoff to max force.
17. Area under the curve of decline from max force to 50% cutoff.

These are example parameters. Parameters 4, 10 and 14 can be measured as duration of rise from various cutoffs to max force during the contraction phase, for example, cutoffs of 10%, 15%, 20%, 25%, 30%, 35%, 40%, 45%, 50%, 55%, 60%, 65%, 70%, 75%, 80%, 85% and 90%. Parameters 5, 11 and 15 can be measured as duration of decline from max force to various cutoffs during the relaxation phase, for example, cutoffs of 10%, 15%, 20%, 25%, 30%, 35%, 40%, 45%, 50%, 55%, 60%, 65%, 70%, 75%, 80%, 85% and 90%. Parameters 6, 12 and 16 can be measured as area under the curve of rise from various cutoffs to max force, for example using cutoffs of 10%, 15%, 20%, 25%, 30%, 35%, 40%, 45%, 50%, 55%, 60%, 65%, 70%, 75%, 80%, 85% and 90%. Parameters 7, 13 and 17 can be measured as area under the curve of decline from max force to various cutoffs, for example using cutoffs of 10%, 15%, 20%, 25%, 30%, 35%, 40%, 45%, 50%, 55%, 60%, 65%, 70%, 75%, 80%, 85% and 90%.

Other parameters can be added without changing the basic methodology. For instance, electrical conduction versus time tracings can provide one or a plurality of additional parameters that can be used instead of or in addition to the foregoing parameters to provide further insights using the methods and apparatuses disclosed herein.

Figure 2:
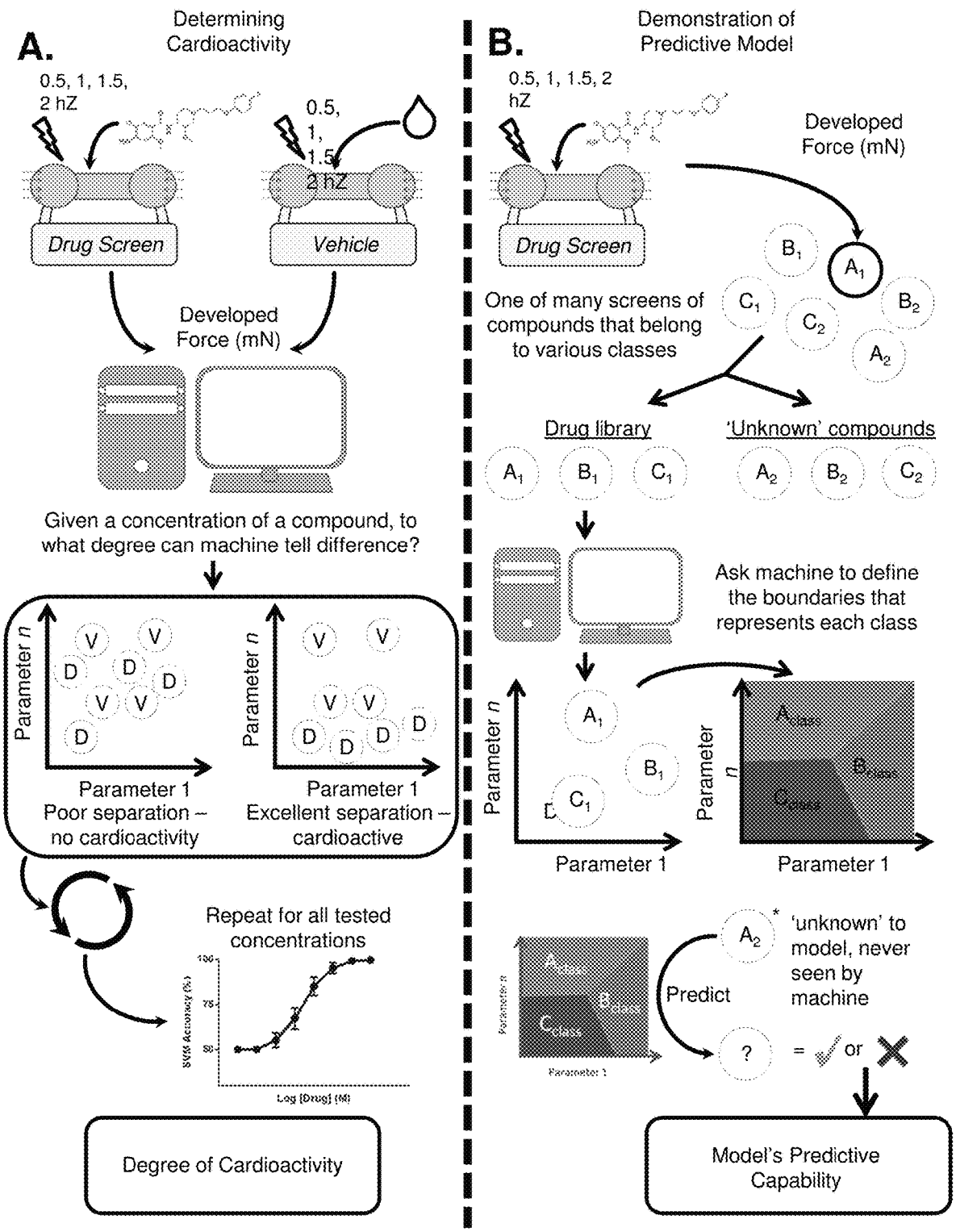
FIG. 2 schematically illustrates systems and methods for determining cardioactivity and predicting mechanistic action. (A) To determine if a concentration of a compound was cardioactive, parameters describing the force waveforms were compared to those of a control, e.g., a vehicle study with a binary SVM approach that generates a singular quantitative index. If the compound does not modulate the contractile behavior of hvCTSs, the generated data points would be similar to those of the vehicle, yielding poor separation and an SVM accuracy of approximately 50%. However if a compound's cardioactive effects become more distinguishable, separation between the two groups becomes more feasible and results in a higher SVM accuracy (100% as maximum distinguishability). This binary SVM approach generates a singular quantitative index that describes the degree of cardioactivity of a given concentration for a drug compound. (B) To create a model for the prediction of mechanistic action, data from screened compounds were divided into two groups, library and 'unknown.' Using data from the library group, the machine defined boundaries that represent various drug families. The model was evaluated for its predictive capabilities by having the machine classify the 'unknown' compounds.

Once the parameters characterizing each contraction were calculated, establishing the library for machine learning consisted of two primary steps. The first step was determining the degree of cardioactivity for each compound at a given dosage by calculating a singular quantitative index generated by a binary SVM approach (FIG. 2, A). The second step involved multi-class SVM to establish boundaries that represent each drug class (FIG. 2, B).

The binary SVM is capable of summarizing all parameters and providing a simple metric that expresses a compound's degree of cardioactivity at a given dosage (Lee et al., 2015). Specifically, the machine is tasked with creating a decision boundary that separates between two groups (data from untreated hvCTSs and those from hvCTSs exposed to a concentration of a compound) as seen in FIG. 2, A. The decision boundary is evaluated for generalizability by classifying withheld data, referred to as a test set. As a result, a SVM accuracy metric is calculated to reflect the machine's ability to identify a cardioactive effect (e.g. 75% accuracy means that out of 100 data points, the machine could correctly classify 75 of them). To account for variations within the data set, multiple runs are performed to calculate the mean SVM accuracy. A value of approximately 50% mean SVM accuracy suggests non-cardioactivity as the machine cannot distinguish between treated hvCTS data from control data, and the classification becomes random. Prominent cardioactive effects allow the space between the data from treated and control conditions to become more distinguishable, leading to a higher SVM accuracy with 100% being the maximum.

The second step was the utilization of multi-class SVM to create and evaluate a model. The eleven compounds (excluding aspirin) were divided into two groups (FIG. 2, B). The first group was referred to as a 'drug library' and used to train a model that defined the boundaries of each drug class. The second group was completely withheld from the computer throughout the entire training and tuning of the model and was referred to as the 'unknown' compounds. To normalize for the varying degrees of cardioactivity among compounds, the concentration of a compound that achieved a metric closest to 85% mean SVM accuracy (see Example 6) was used in the formation and evaluation of the model. To ensure that the library was generalizable or had the capability to classify itself, a subset of the first group's data, a test set, was randomly withheld from the computer prior to training. The library was evaluated on its performance to accurately identify this test set. Afterwards, the library was asked to predict the 'unknown' compounds and its performance was evaluated for predictive capabilities. To account for the variation and random selection of training and test sets, the creation and evaluation of the models were performed 50 times.

Control Experiments

Figure 3:
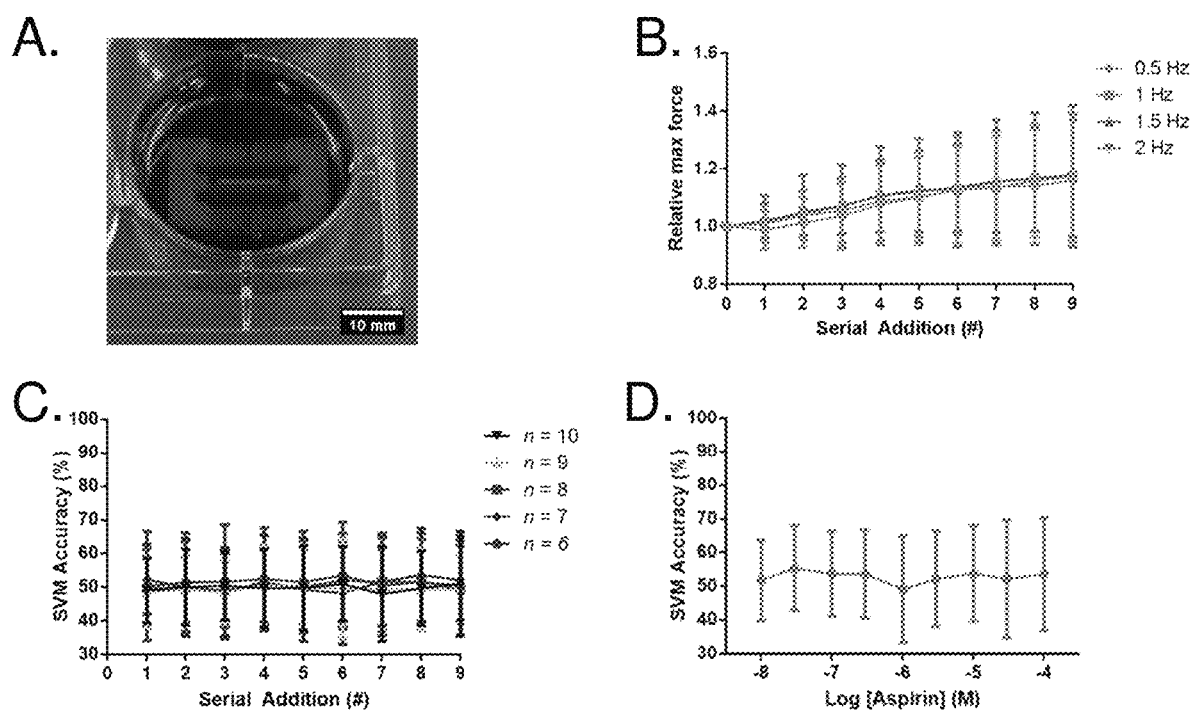
FIG. 3 illustrates control experiments and screening of non-cardioactive compound. (A) hvCTSs were formed by the compaction of hPSC-CMs, fibroblasts, and extracellular matrix solution around two posts comprising PDMS. Force data were derived from the deflection of posts. (Scale bar=10 mm) (B) hvCTSs of the vehicle study exhibited a drift in contractile behavior after serial additions of water (n=28). (C) To normalize for shift, data from each drug condition was compared to its respective vehicle condition (matching serial addition number). With this, a benchmark of non-cardioactivity was created with subsets of vehicle-treated strips being modeled as strips exposed to non-cardioactive compounds and compared to other vehicle-treated strips with binary SVM. The number of tissue strips in the subset (n=6-10) had no effect as SVM accuracies were approximately 50% for all conditions. (D) To assess non-cardioactivity benchmark, the data of aspirin-treated hvCTSs indicated no statistical difference from the vehicle study over the tested range (n=6).

Although the hvCTSs (FIG. 3, A) were examined under temperature-controlled conditions, there was an observable drift in contractile behavior of the vehicle-treated hvCTSs. For example, the relative measured maximum developed force increased for all pacing frequencies by a cumulative average of 16.96±0.83% upon the ninth serial addition (FIG. 3, B). To account and normalize for baseline drift, each drug condition was compared to its respective vehicle condition via binary SVM (e.g., measurements of the $7^{th}$ serial drug addition were compared to those of vehicle-treated hvCTSs at the $7^{th}$ serial addition). To establish a benchmark of non-cardioactivity, a subset of the vehicle-treated hvCTSs were randomly selected to model a non-cardioactive compound. Binary SVM was then performed between the subset and a corresponding control group of equal size (n).

To ensure that the number of hvCTSs in the subset had no effect, the calculations were performed with the sample size, n, equal to 6-10, which matched the range of numbers of strips used in each drug study of the 12 tested compounds. As expected, the SVM accuracy, regardless of the size of n, was approximately 50% for all serial additions (FIG. 3. C). These results indicated that there were no consistent and distinguishable trends within each serial addition and therefore a reference of non-cardioactivity was created.

To validate this reference of non-cardioactivity, drug screens of aspirin from the database were used as negative controls. Aspirin is known to have no cardioactive effects on hPSC-CMs (Lu et al., 2015; Maddah et al., 2015; Scott et al., 2014). The SVM accuracies of the aspirin drug screens (n=6) had an average of 52.85±1.77% among all serial additions (10 nM to 100 μM). None of the conditions were statistically different from vehicle counterparts, indicating non-cardioactivity by aspirin (FIG. 3, D).

Generalizability of Drug Classification Model

Figure 4:
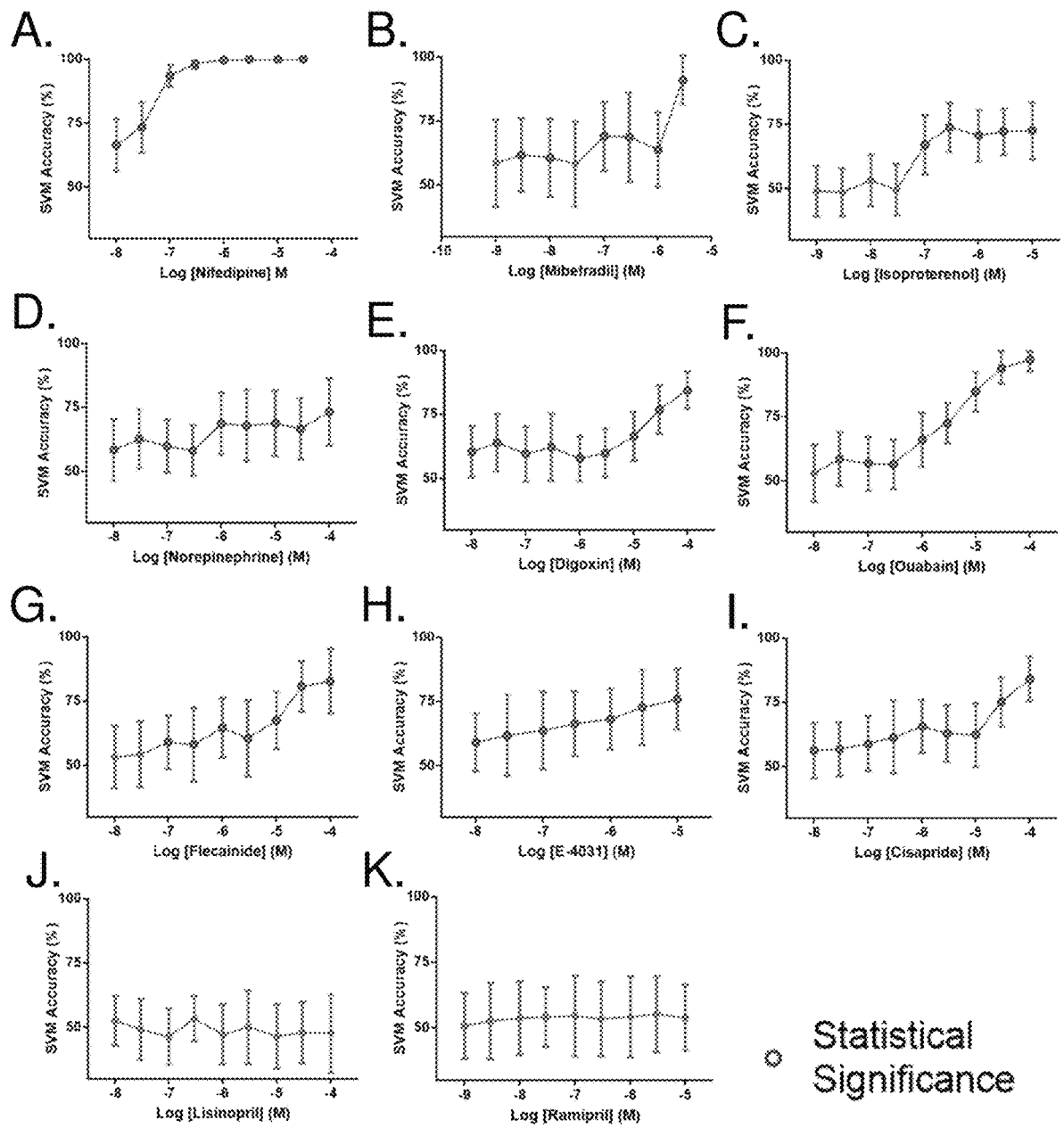
FIG. 4 illustrates the implementation of binary SVM to determine cardioactive effects of 11 compounds, including: (A) nifedipine ($p<0.0063$; n=10), (B) mibefradil ($p<0.0063$; n=6), (C) isoproterenol ($p<0.0055$; n=10), (D) norepinephrine ($p<0.0055$; n=8), (E) digoxin ($p<0.0055$; n=9), (F) ouabain ($p<0.0055$; n=10), (G) flecainide ($p<0.0055$; n=8), (H) E-4031 ($p<0.0071$; n=8), (I) cisapride ($p<0.0055$; n=9), (J) lisinopril ($p<0.0055$; n=8), and (K) ramipril ($p<0.0055$; n=7). Open circles indicate statistical significance in comparison to vehicle-treated hvCTSs. p-values are adjusted with a Bonferroni correction.

In setting up the drug classification model, the eleven non-reference compounds were compared to vehicle-treated tissue strips with the aforementioned binary SVM approach. At one or more of the tested concentrations, all but two compounds, lisinopril and ramipril, had SVM accuracies that were significantly greater than those of the respective vehicle studies (FIG. 4). The ACE inhibitors, lisinopril and ramipril, did not have detectable cardioactive effects on hvCTS contractility, consistent with the results of other platforms (Harmer et al., 2012; Scott et al., 2014). Therefore, the ACE inhibitor class was removed from the library resulting in a four-class system. Mibefradil, norepinephrine, ouabain, and cisapride were chosen to represent the 'unknown' compound group on which the model would make de novo predictions. Mibefradil and cisapride were of particular interest because both compounds had received market approval and were subsequently withdrawn (Li et al., 2016). Nifedipine, isoproterenol, and digoxin were chosen to represent the $Ca^{+2}$ channel blocker, adrenergic agonist, and cardiac glycoside classes respectively. As both flecainide and E-4031 have known hERG $K^+$ channel blocking capabilities, the impact of having either compound represent the hERG $K^+$ blocker family was evaluated by generating the multi-class model under three different conditions: 1) flecainide only, 2) E-4031 only, and 3) both flecainide and E-4031.

Figure 5:
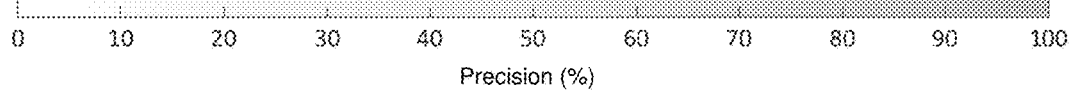
FIG. 5 illustrates the generalizability of drug classification models with varying representative compound(s) for the hERG $K^+$ channel blocker family. (A) Condition 1: Flecainide. Generalizability was evaluated by having the model classify a withheld test set composed of compounds used to define the library. (Left panel) The confusion matrix displays the average number of classified contractile events over 50 runs and is imposed with a color scale that indicates precision rate. "Runs" refers to discrete computer simulations involving different randomly selected groupings of test sets and library. (Right panel) Summary of metrics evaluating performance. $F_1$ scores are above 0.6 for all classifiers, indicating good predictability. (B) Condition 2: E-4031. (Left panel) Confusion matrix indicates that all compounds were being correctly classified to themselves as the diagonal of the matrix had the highest precision rate. (Right panel) Metrics indicate similar performance between Condition 1 and 2. (C) Condition 3: Flecainide and E-4031. (Left panel) Confusion matrix indicates no major effect on generalizability by having two compounds define a class. (Right Panel) Similar to condition 1 and 2, $F_1$ scores are all above 0.6 indicating good generalizability of model.

A subset of the data was always withheld from the machine prior to training in each of the runs. This withheld set quantified the generalizability in the models and ensured that overfitting had not occurred. Upon asking the machine to classify these test sets, the multi-class models demonstrated good generalizability by being able to correctly classify itself at an average accuracy rate of 76.09±6.43, 78.29±5.34, and 73.61±5.19% for the flecainide only, E-4031 only, and flecainide & E-4031 conditions respectively (FIG. 5).

In all three conditions, the multi-class models behaved similarly in that both the nifedipine and isoproterenol classifiers performed the best by always achieving the highest $F_1$ score values, a metric that ranges from 0 to 1 with 1 representing perfection in model's classification. This performance indicates that the data points of the nifedipine and isoproterenol compounds occupied very distinct boundaries compared to the other two classes, allowing for the binary learners to more accurately separate these compounds from others. For perspective on the quality of model performance, if there were no discernable differences among the four compounds for the machine to use, the expected values for precision (i.e., positive predictive value), recall (i.e., sensitivity), and accuracy would be a rate of 25% with a $F_1$ score of 0.25. As all three multi-class models demonstrated good generalizability with average accuracy rates exceeding 70%, these results suggest the setup of the model was robust to the choice of compound representing the hERG $K^+$ channel blocker family.

Prediction on 'Unknown' Compounds

Figure 6:
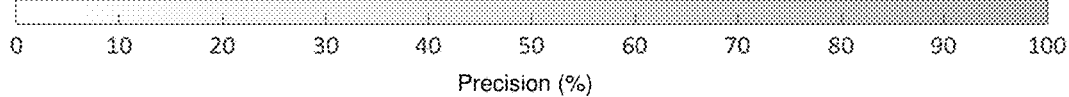
FIG. 6 illustrates the predictability of drug classification libraries with varying representative compound(s) for the hERG $K^+$ channel blocker family. (A) Condition 1: Flecainide. Libraries of all three conditions were evaluated for capabilities to predict drug families of compounds previously unseen by the machine. (Left panel) Confusion matrix displays the average number of predicted contractile events from 'unknown' group over 50 runs. 'Unknown' compounds were classified to correct drug family as the precision rate was highest along the diagonal of matrix. (Right panel) Model demonstrated good predictability as the macro-average of $F_1$ score was 0.71. (B) Condition 2: E-4031. (Left panel) Cisapride was predominantly mislabeled as a member of cardiac glycoside family, represented by digoxin. Other three compounds were classified correctly to their respective drug families. (Right panel) The classifier of hERG $K^+$ channel blocker class had a F1 score of 0.27. As the other three classifiers maintained a $F_1$ score above 0.6, E-4031 did not define boundaries similar to that of cisapride. (C) Condition 3: Flecainide and E-4031. (Left panel) Precision rates are highest along the diagonal of matrix. (Right panel) The model yielded good predictability and was not impacted by the inclusion of E-4031 data to that of flecainide.

With each condition's model established and evaluated, the machine was then asked to predict the data from the 'unknown' compounds group. In the first scenario with flecainide as the only hERG $K^+$ channel blocker representative, the multi-class model was able to correctly assign the four 'unknown' compounds to their corresponding counterparts with an average accuracy of 71.69±1.96% (FIG. 6, A). The four binary classifiers of this model demonstrated overall predictability by all having an average $F_1$ score above 0.6.

When the second drug class model (only E-4031 defining hERG $K^+$ channel blocker class) was used to predict the 'unknown' compounds, the average accuracy diminished to 65.37±2.33% (FIG. 6, B). This decrease was mainly the result of the contractile events from hvCTSs exposed to cisapride being miscategorized. Of the 779 contractile events from hvCTSs exposed to cisapride, on average, 46.76±7.00% of the events were incorrectly labeled as hvCTSs affected by a cardiac glycoside. These misclassifications yielded a poor precision rate, 20.51±11.20%, and subsequently, a low $F_1$ score, 0.27±0.11, for the hERG $K^+$ channel blocker classifier. As for the classifiers of the other three families, they performed comparably to those of the first condition and all had an average $F_1$ score over 0.6. These results indicate that using only data of hvCTSs exposed to E-4031 is not sufficient for defining the hERG $K^+$ channel blocker family within a multi-class model and enabling that model to correctly predict cisapride's mechanistic action on cardiac tissue contractility.

In the last condition where the machine was trained with both flecainide and E-4031 representing the hERG $K^+$ channel blocker family, the average accuracy was 71.43±2.09% (FIG. 6, C). All four classifiers had an average $F_1$ score higher than 0.6. Unlike the second condition, the hERG $K^+$ channel blocker classifier had a precision rate higher than 25% at 66.87±8.05%. Similar to that of the first condition, the macro-average of the $F_1$ scores for this multi-class model was 0.71, demonstrating good predictability. These results suggest that the data points from the hvCTSs exposed to flecainide designated boundaries within the model that was similar to those of cisapride-treated hvCTSs. Finally, the inclusion of E-4031 data with the flecainide data did not negatively impact the multi-class model's ability to correctly predict cisapride's mechanistic action as neither the precision rate nor the recall rate fell below 41% as they did in the second condition.

Class Relationship Metrics

Figure 7:
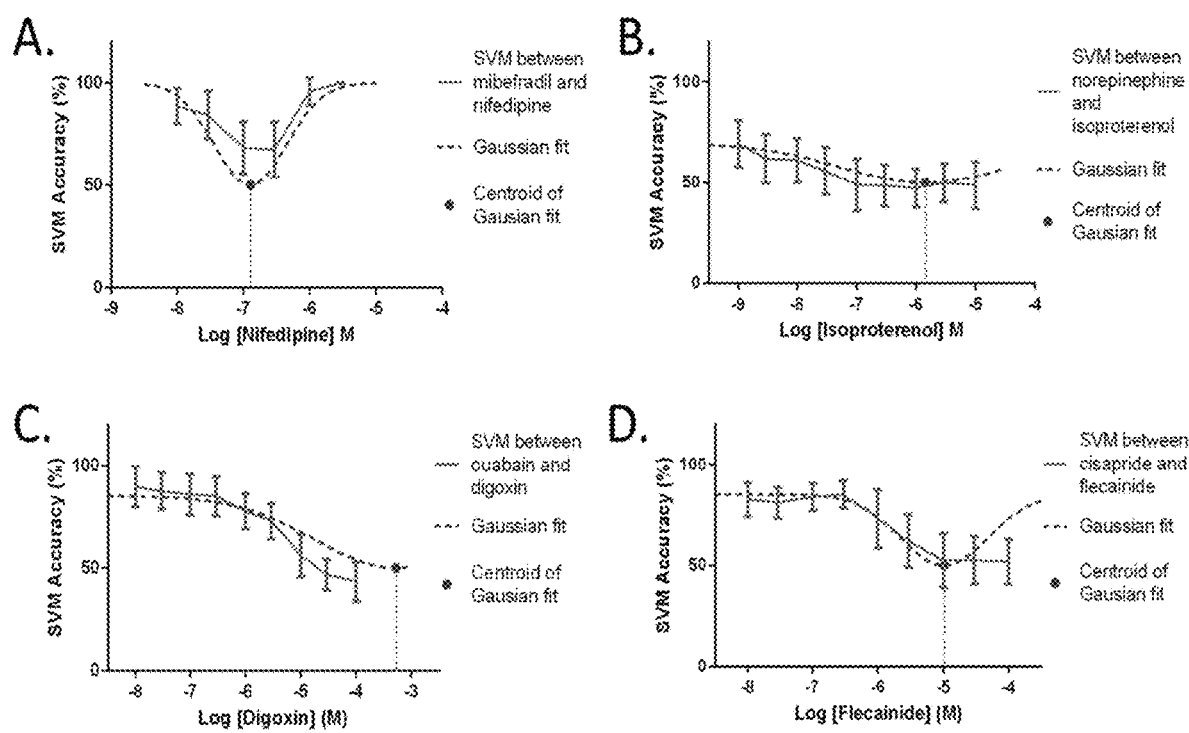
FIG. 7 illustrates the drug response relationships of 'unknown' compounds to compounds representing predicted classes using a binary SVM approach. Solid line indicates the binary SVM accuracy between a concentration of the 'unknown' compound and each tested concentration of the representative compound. Dotted line indicates a fitted Gaussian curve where the centroid represents the concentration at which the representative compound elicits the most similar response in the hPSC-CMs as the condition of the 'unknown' compound. (A) mibefradil and nifedipine ($Ca^{2+}$ blockers), (B) norepinephrine and isoproterenol (adrenergic agonist), (C) ouabain and digoxin (cardiac glycoside), and (D) cisapride and flecainide (hERG $K^+$ channel blocker).

Once the drug classes were predicted, the concentrations of library compounds that induced the most similar cardioactive effects as the 'unknown' compounds were computed (FIG. 7; protocol in Example 5). These relationship metrics are summarized in Table 2.

TABLE 2

Summary of estimated drug response relationships of all four classes.

| Compound (M) | Predicted Class | Estimated Similar Concentration (M) |
|---|---|---|
| Mibefradil (3.0 × 10$^{-6}$) | Ca$^{2+}$ channel blocker | Nifedipine (1.28 × 10$^{-7}$) |
| Norepinephrine (1.0 × 10$^{-5}$) | Adrenergic agonist | Isoproterenol (1.44 × 10$^{-6}$) |
| Ouabain (1.0 × 10$^{-5}$) | Cardiac glycoside | Digoxin (5.35 × 10$^{-5}$) |
| Cisapride (1.0 × 10$^{-4}$) | hERG $K^+$ channel blocker | Flecainide (1.03 × 10$^{-5}$) |

For example, an estimated 5.35×10$^{-5}$ M of digoxin would be needed to evoke a level of cardioactivity that matches ouabain tested at 1.0×10$^{-5}$ M. Such relationships could provide insights about drug potency. In the aforementioned example, ouabain would be considered the more potent compound as it requires approximately 5-fold lower concentration to achieve the same level of cardioactivity. Ouabain's higher potency has been observed in other in vitro studies (Guo et al., 2011; Katz et al., 2010).

Decoupling Force Frequency Relationship

Figure 8:
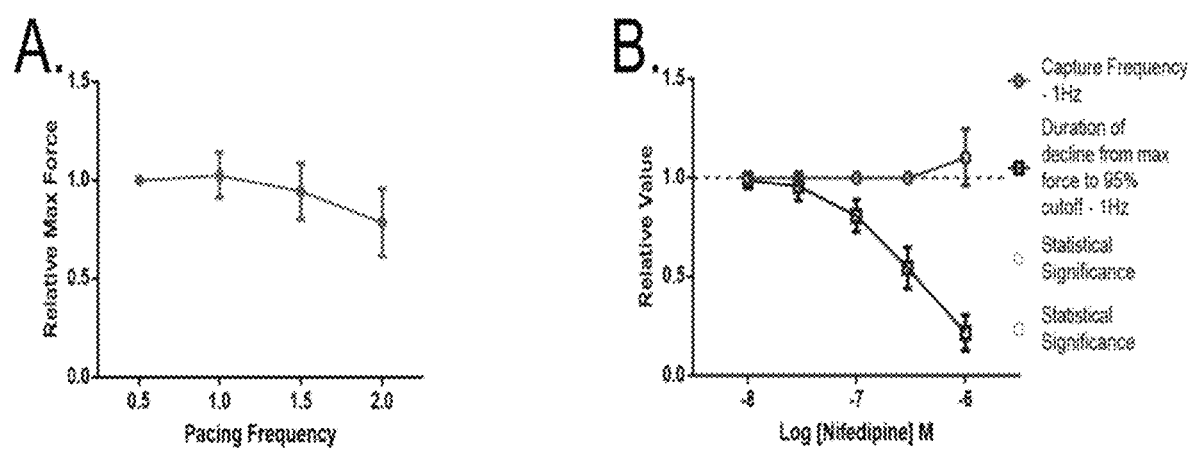
FIG. 8 illustrates an experimental confirmation of nifedipine's inotropic effects. (A) Force-frequency relationship of vehicle-treated hvCTSs. (B) Nifedipine-treated hvCTSs had capturing frequencies that matched the pacing frequency of 1 Hz from $1.0\times10^{-8}$ to $3.0\times10^{-7}$ M. During this range, the max force generated decreased by 45.69+10.42%. Since the force-frequency relationship was decoupled by pacing the strips, it can be concluded that the decrease in force is attributed to the compound's negative inotropic effects ($p<0.0063$; n=10).

While the concept of examining multiple parameters from waveforms has been pursued lately, some studies have suggested that only a few select parameters (e.g., peak count) are necessary in assessing a compound's cardioactivity as other parameters provide no further mechanistic insight (Lu et al., 2015; Pointon et al., 2016; Sirenko et al., 2013). This is primarily true when the hPSC-CMs are spontaneously beating, meaning the force generated is linked to beating frequency. This study's dataset affirmed the importance of decoupling this force-frequency relationship through the pacing of the tissues. By setting a fixed pacing frequency, any changes to the force waveform can be truly accredited to a compound's inotropic and lusitropic effects. For example, if the nifedipine-treated strips were allowed to spontaneously beat, a positive chronotropic effect would have most likely been observed (Guo et al., 2011; Harris et al., 2013; Pillekamp et al., 2012). As the hvCTSs displayed a negative force-frequency relationship (FIG. 8, A), a decrease in maximum developed force could not be directly linked to either chronotropic or inotropic effects. When 0.3 µM nifedipine-treated hvCTSs were paced at 1 Hz, the captured frequency of the tissue was 0.99±0.01 Hz and the maximum developed force decreased by 45.69±10.42% (FIG. 8, B). This paced data confidently confirmed nifedipine had a negative inotropic effect.

Examination of Cardioactive Effects

The data was further examined on an individual parameter basis to better comprehend the performance of the multi-class models and their ability to differentiate between different mechanistic actions. The adrenergic agonists and cardiac glycosides were expected to induce a positive inotropic response in the hvCTSs, while the Ca$^{2+}$ and hERG K±channel blockers would induce a negative inotropic response. The negative inotropic agents prompted distinct decreases in maximum force generated among hvCTSs; however, the hvCTS sensitivity to positive inotropic agents was not very apparent. For example, hvCTSs exposed to 10 µM of isoproterenol and paced at 0.5 Hz had a similar increase in maximum developed force to that of respective vehicle-treated strips (10.42±16.23% and 15.76±21.05%, respectively), suggesting the compound had negligible inotropic effects (FIGS. 9, A & B) (Turnbull et al., 2014). Rather, isoproterenol's cardioactive effects manifested in other parameters. For example, the duration of the relaxation phase or time from maximum developed force to 95% cutoff decreased by 22.19±19.35% for the strips exposed to 10 µM isoproterenol, while those of the vehicle-treated strips experienced essentially no change. Thus, through the various parameters, machine learning was able to leverage the positive lusitropic effects in both binary and multi-class SVM to distinguish the adrenergic agonist class.

Cardiac glycosides-treated hvCTSs also demonstrated the system's sensitivity to positive inotropes. Typically, these compounds increase the waveform amplitude (Ca$^{2+}$ transients or microelectrode array measurements); however, in this dataset, the hvCTSs decreased in maximum developed force as the concentration increased (FIG. 9, C) (Dempsey et al., 2016; Ravenscroft et al., 2016). Such results could be attributed to cardiac glycoside toxicity or immature phenotype. Studies have shown that above 3 µM of digoxin or ouabain monolayers of hPSC-CMs stopped beating (Dempsey et al., 2016; Guo et al., 2013; Sirenko et al., 2013). In this dataset, the highest concentration applied for both cardiac glycosides was 100 µM. At 100 µM of ouabain, 4 of the 10 treated strips stopped beating at all pacing frequencies.

Figure 9:
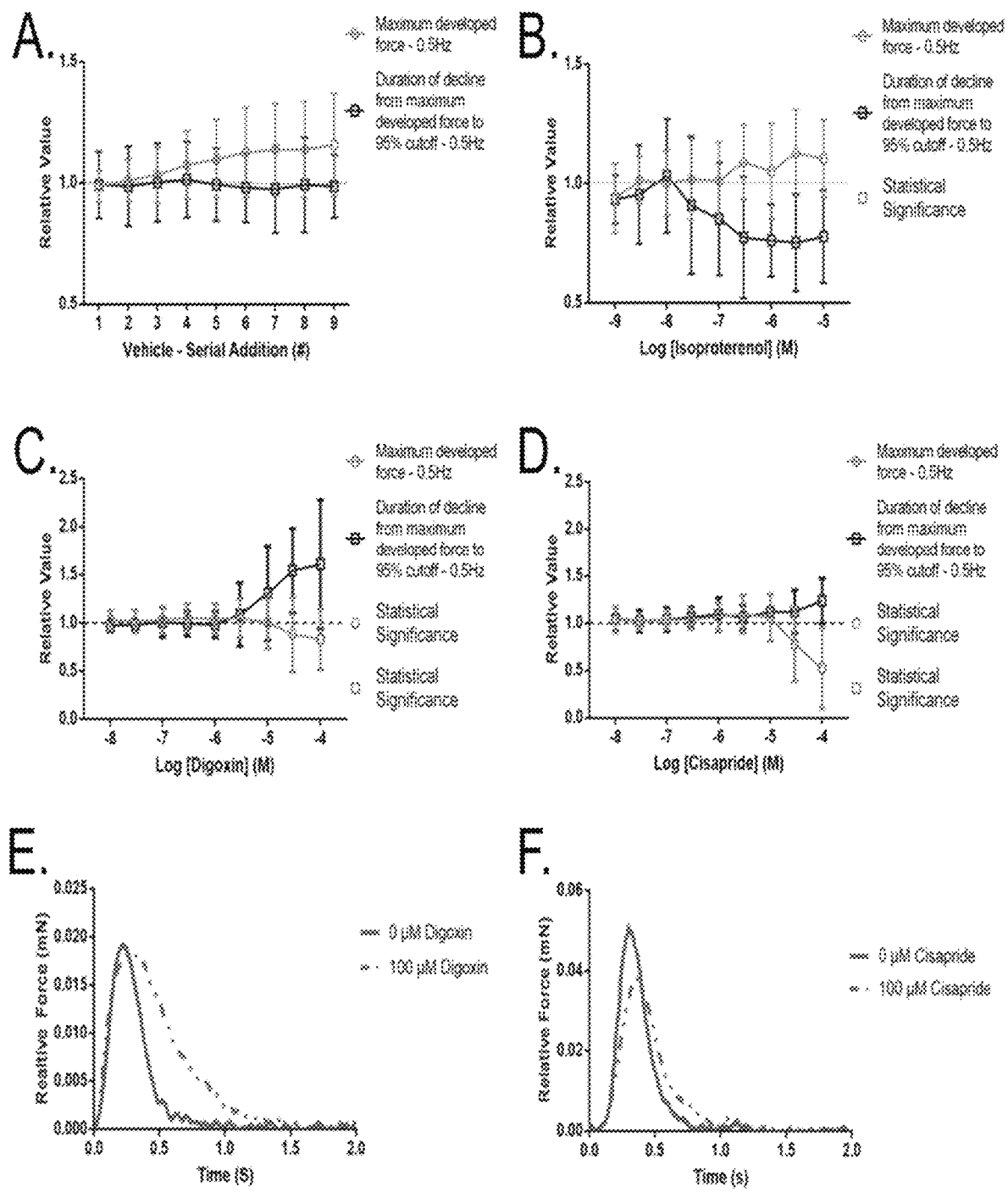
FIG. 9 illustrates an examination of various compounds' cardioactive effects. (A) In the vehicle study, hvCTSs paced at 0.5 Hz continually increased in maximum developed force through subsequent serial additions. The duration of decline from max force to 95% cutoff, relaxation phase, was unaffected by the number of serial additions. (n=28). (B) Isoproterenol-treated hvCTSs experienced an increase in max force similar to the vehicle-treated strips, suggesting no inotropic effects. Isoproterenol's lusitropic effects were apparent as duration of the relaxation phase decreased significantly versus the vehicle study over a concentration range of $3.0\times10^{-7}$ to $10^{-5}$ M ($p\leq0.0055$; n=10). (C) Digoxin-treated hvCTSs (paced at 0.5 Hz) exhibited a decrease in max force and an increase in duration of relaxation phase by the highest concentration, $10^{-4}$ M ($p\leq0.0055$; n=9). (D) Cisapride-treated hvCTSs (paced at 0.5 Hz) exhibited similar trends to that of the digoxin-treated hvCTS in max force and duration of relaxation phase by the highest concentration, 100 μM ($p<0.0055$; n=9). (E) Representative force tracing of a contractile event from a digoxin-treated hvCTS (paced at 0.5 Hz) shows the distinct cardioactive effects prolonging the duration while increasing the area under the curve of the relaxation phase. (F) Representative force tracing of a contractile event from a 100 μM cisapride-treated hvCTS (paced at 0.5 Hz) shows that while cisapride and digoxin have similar trends in certain parameters, the cardioactive effects of the two are visibly distinguishable. All listed p-values are adjusted with a Bonferroni correction.

Like those of isoproterenol, cardioactive effects of the cardiac glycosides at lower concentrations appeared in other parameters. When either the concentration of cisapride or digoxin increased, the maximum developed force decreased while the duration of the relaxation phase increased (FIGS. 9, C & D). If limited to the observation of only these two parameters, one might conclude that cisapride and digoxin are related. But upon visual inspection of the force traces, it is evident that the compounds have distinct effects on hvCTSs and mechanistic actions (FIGS. 9, E & F). Changes in these parameters were clearly unique to the cardiac glycoside family as the ouabain-treated strips were correctly predicted from the other three classes.

Discussion

In recognition of the need for better detection of drug-induced cardiotoxicity, numerous methodologies have emerged to capture and quantify the attributes of hPSC-CMs when exposed to cardioactive compounds, ranging from phenotype to calcium transients to contractile force. The nature of this outputted data becomes high-dimensional when multiple experimental conditions are present or a multiplex system is used (Dempsey et al., 2016). In this study, we present the use of supervised machine learning to exploit high dimensional data and provide relevant information in an automated manner. Besides indicating if a compound was cardioactive, the machine constructed a multi-class drug model that accurately classified cardioactive compounds that it had never previously encountered. This comprehensive approach can be readily applied to other screening platforms to more fully utilize generated datasets and enhance evidence-based decision-making for drug development.

With multi-class SVM, drug classification libraries were established under various conditions to examine effects on predictive performance. The conditions that yielded the best performance in predicting mechanistic action were the two libraries that included flecainide as a representative of the hERG $K^+$ channel blocker family. In both libraries, the macro-averages of $F_1$ scores were 0.71 (macro-average of $F_1$ scores would be 0.25 if random classifiers were used). While this clear difference in $F_1$ scores indicates that the models have the capability to predict a compound's mechanistic action, there are opportunities to further improve model performance and obtain $F_1$ scores closer to 1, indicating reduction in errors.

One method to improve model performance is to define each drug family with multiple compounds. By having only one compound define a class, there is a risk of only defining a partial region of space that the drug class truly encompasses. The data of E-4031 exemplified this when it was tasked with defining the hERG $K^+$ channel blocker family. E-4031's defined boundaries did not match or include that of cisapride's, another hERG $K^+$ channel blocker, causing classification of cisapride to be closer to that of the cardiac glycoside family. The inclusion of flecainide, a mixed hERG $K^+$ channel blocker, with E-4031 in the definition of the class allowed for the correct prediction of cisapride without adversely affecting the predictive capability of the remaining classes. Although the addition of E-4031 to the hERG $K^+$ channel blocker definition does not necessarily improve the predictive capability with respect to cisapride classification, establishing a more expansive region of space to define the hERG $K^+$ channel blocker class may improve prediction of other unknown hERG $K^+$ channel blockers that have effects more similar to E-4031 than flecainide. These results also suggest the potential of having subgroups within classes of the model, which can be achieved through a series of multi-class classifications. For instance, a compound can be predicted as a $Ca^{2+}$ channel blocker in the first classification; within this family, the compound can be subsequently categorized into a subgroup (e.g., defined by frequency-dependent cardioactivity). As machine learning does not define drug classes with a priori knowledge (e.g. guidelines on how parameters are expected to change), the number of drug families and subclasses that can be defined within a model are not limited. The unbiased and automated nature of machine learning is also advantageous when a new drug family needs to be added, because no rubric needs to be manually amended and re-evaluated.

This study demonstrates the potential of machine learning for providing insights in the detection of cardioactivity using hPSC-CMs. The basis of this study's libraries was an error-correcting output codes approach with binary learners being SVM. Different binary learners, such as decision trees, should be explored alongside completely different approaches (e.g., neural networks). The ideal machine learning technique should balance predictive capabilities and use of computational resources. In this study, all models were generated with a standard desktop. Each calculated instance of a model took approximately four hours. However once all models were formed, the predictions made on 'unknown' compounds were on the timescale of seconds.

Improvements of the multi-class drug libraries can also be achieved from enhancements of the hvCTSs and acquisition system. In particular, the sensitivity of this system to positive inotropic compounds can be increased by addressing two issues, the maturity of stem-cell derived cardiomyocytes and the drifting baseline of vehicle-treated strips. Studies have shown that hPSC-CMs elicit a minimal to non-existent response to certain positive inotropic compounds, such as beta-adrenergic agonists, because of immature intracellular structures (Lundy et al., 2013; Pillekamp et al., 2012). When these diminished responses are paired with a baseline that has increasing contractility over time, positive inotropic effects of a compound can get masked and harder to detect as seen in the aforementioned isoproterenol drug screen. While hvCTSs were arranged in an aligned manner and co-cultured with fibroblasts, they can be further matured through additional techniques, such as conditioning by electrical stimulation, a cellular tri-culture including endothelial cells, or forced expression of selected proteins (Eng et al., 2016; Liu et al., 2009; Ravenscroft et al., 2016). As for stabilization of the baseline, different components of the setup, ranging from pH to $CO_2$ levels in ambient environment, should be re-evaluated to minimize overall drift during serial additions. Increasing the system's sensitivity to positive inotropic agents would yield even more distinct boundaries and subsequently better predictability in the drug classification libraries.

In summary, we present the implementation of supervised machine learning on high dimensional data of hvCTSs exposed to drugs while paced at various frequencies. In an automated fashion, this machine learning approach is able to not only determine if a compound is cardioactive, but it can predict the mechanistic action along with other metrics. Furthermore, this approach can be adapted to state of the art tissue engineered cardiac models, including different forms of signals (e.g., calcium transients, micro electrode array and optical recordings), and has the potential to integrate diverse output data of multiplex systems or even those across platforms. Along with analyses of compounds with acute cardioactive effects, machine learning can be readily applied with non-invasive techniques (e.g., force calculation with hvCTS) to longitudinal studies to inspect a compound's chronic effects. Moreover, machine learning can be utilized on a grander scale by incorporating past clinical data to determine the optimal combination of in vitro and in silico data for the prediction of drug-induced cardiotoxicity in patients.

Software

The software utilized enables the use of readouts of cardiac tissue strips or other models of human myocardium to provide relevant information about a compound's cardioactivity potential for the streamlining of the drug discovery pipeline.

The software utilizes machine learning to analyze the curves or shapes of each contractile events (cardiac beats) acquired from a screening platform's readout. To describe these curves or shapes, parameters are derived (e.g., amplitude). For example with the human ventricular cardiac tissue strips, 17 parameters are calculated from the force readouts. The machine learning is able to simultaneously analyze all parameters and any underlying relationships. Using machine learning we generate a singular quantitative index that determines a compound's level of cardioactivity. This is achieved by comparing the readouts of each drug concentration to readouts of cardiac models at a control state. The control tissues could be either healthy or diseased, allowing the added possibility of using disease models to screen for disease-specific cardioactivity. If the compound is deemed cardioactive, we can then predict the mechanism of cardioactivity with a library of defined drug classes. Since machine learning is implemented, guidelines and rubrics that define a drug class are not required. This allows for the addition of drug class into the library with relative ease. Furthermore, drug response relationships between compounds can be determined (e.g., what concentration of Compound A is required to elicit the same response at a concentration of Compound B).

The relevant information mentioned above assists researchers in more efficient drug development. The prediction of a drug compound class allows for the rapid identification of select compounds for more in-depth follow up assays. In addition, this information coupled with knowledge of predicted class guides scientists to efficiently and selectively screen for specific drug-to-drug interactions that prompt cardiotoxicity (e.g., disruption of $Ca^{2+}$ handling when sofosbuvir and amiodarone are combined) instead of a brute force approach. Collectively, the information enables better evidence-based decision-making in drug development. Applications include, but are not limited to, drug screening and basic research of cardiomyocytes.

Software takes into account hardware requirements, operating system requirements, programming language (e.g., MATLAB), user interfaces, drawings, schematics and flow charts, required utilities, required distribution format(s), and significance of third party code.

In some embodiments, the software is used for drug screening and toxicity studies.

The concept of integrating parameters derived from an assay or across multiple assays has been explored. Software tools such as ToxPi analyze and weight different inputted data. Other studies, such as Clements et al. ('Bridging functional and structural cardiotoxicity assays using human embryonic stem cell-derived cardiomyocytes for a more comprehensive risk assessment' Toxicological Sciences, 2015), have clustered compounds into groups by integrating data of multiple assays (e.g., functional readouts of microelectrode arrays paired with structural readouts of high content analysis). The software described here is able to integrate the data of multiple parameters derived from a single or multiple assays and create a drug classification library in an automated manner. The establishment of this library does not require any guidelines, rubrics or thresholds (e.g., a compound is deemed chronotropic if the beating frequency exceeds 20% of that of healthy cardiomyocytes). The library is then able to predict the mechanism of cardioactivity of unknown compounds (those never seen by the computer), which is not evidently present in the aforementioned software and studies. In addition, this software is adaptable to various readouts of different screening platforms.

Example 1 hvCTS Formation

Human ventricular cardiomyocytes were differentiated from a hES2 stem cell line with a Wnt inhibitor-based protocol as previously described (Weng et al., 2014). Human ventricular cardiac tissue strips (hvCTS) were then formed by mixing cardiomyocytes (100 k cells per strip) at 14-16 days post differentiation with a solution of bovine collagen I (2 mg/mL), Matrigel (0.9 mg/mL), and human foreskin fibroblasts (100 k cells per strip) as previously described (Turnbull et al., 2014). The cell-matrix solution (100 uL per tissue strip) was injected into a custom PDMS force-sensing bioreactor device and placed in an incubator (37° C. and 5% $CO_2$). Formed hvCTSs were fed DMEM with 10% new born calf serum, 1% penicillin-streptomycin and 0.1% amphotericin B. The PDMS device contains two flexible vertical end-posts to which the tissue anchors, causing the posts to deflect as the tissue beats. Contractile force measurements were captured with a high speed (100 fps) CCD camera while custom LabVIEW software tracked the centroid movement of the flexible post tips. Force was converted from the deflection of the PDMS posts by an elastic beam bending equation (Serrao et al., 2012). A custom MATLAB script was used to calculate 17 parameters that described the overall shape of the force traces for each contractile event (FIG. 1). Each contraction was regarded as an individual data point for the machine learning analysis.

Example 2

Drug Treatment

After 7-8 days post tissue formation, hvCTS were exposed to drugs for pharmacodynamic analysis. Flecainide, lisinopril, norepinephrine and ramipril were provided by Pfizer, while all other compounds were purchased form Sigma-Aldrich. Compounds were initially resuspended in DMSO and subsequently diluted in water for final concentrations composed of less than 0.1% (vol/vol) DMSO. The PDMS device containing the hvCTS was placed onto a heated stage (37° C.) under a dissecting microscope. Before either vehicle or drug addition, the media was replaced with DMEM containing high glucose (4.5 g/L) and HEPES without phenol red. Drug doses were added to a tissue in consecutively increasing manner up to 10 concentrations with 3 minutes in between measurements. Vehicle doses containing only water were applied similarly. A pulse stimulator (AMPI Master-9) connected to platinum wires electrically paced the hvCTS with a monophasic electric field of 5 V/cm with a 10 ms pulse duration.

Example 3

Machine Learning

Figure 10:
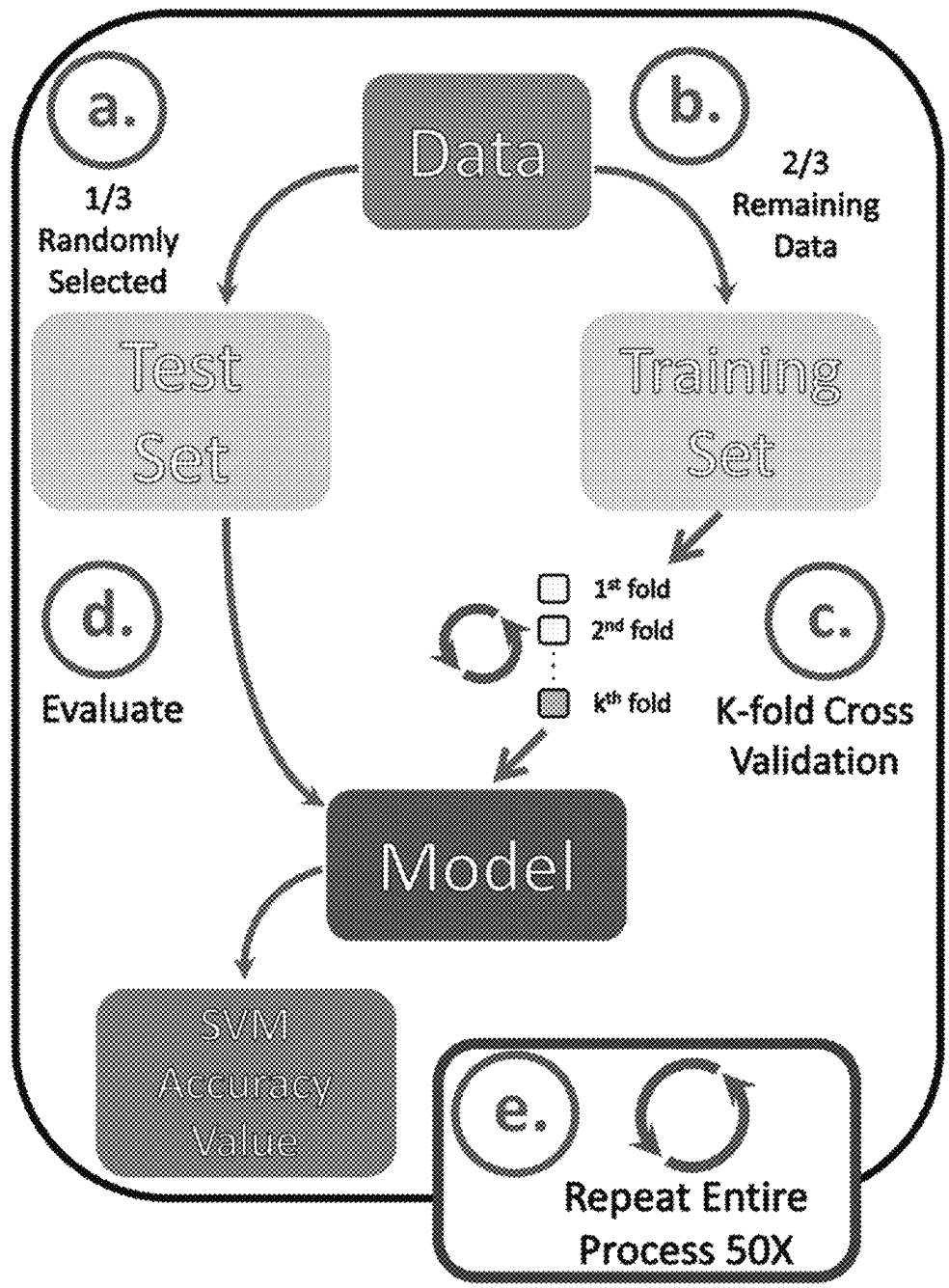
FIG. 10. Process flow of how SVM accuracy value is generated. (A) Prior to any model training or formation, a portion of, e.g., one third of, the data is randomly withheld as the test set. (B) The remaining data is referred to as the training set and used to create a model. (C) To prevent overfitting, a K-fold cross validation is performed. (D) The model is than evaluated by having it label the data of the withheld test set. This evaluation leads to a SVM accuracy value. (E) As the data is randomly selected for the test set, the process is repeated 50 times to account for any variation.

To establish the drug class model, we identified individual compounds that respectively represented our defined classes. The compounds and the corresponding tested concentrations are listed in Table 1. To determine which concentration of a chosen compound to add to the model, we first gauged each compound's level of cardioactivity by utilizing binary SVM (FIG. 10) (Lee et al., 2015). To normalize for the increasing variation seen in hvCTS contractile behavior during the later serial additions of the vehicle studies, the SVM was performed between each concentration of a compound and the vehicle data from the corresponding serial addition number in which the concentration was achieved (FIG. 2, A). Details of optimizing SVM classifiers are discussed in Example 6.

For multi-class classification, we then selected the compound concentration that met two criteria: 1) a binary SVM accuracy closest to 85% and 2) at least 6 of all screened tissue strips were still responsive to electrical stimulation (see Example 6). As seen in FIG. 2, B, we then divided the compounds into two groups, one used to train the multi-class model and one representing 'unknown' compounds to be predicted. During this separation it was ensured that each class was at least represented by one compound within the two groups. For training of the model, we used an error-correcting output codes approach with the binary learners being SVM (Dietterich, 1995). To confirm generalizability of the generated models, we randomly pre-allocated a third of the data as a test set prior to the training. Finally, we evaluated the multi-class model with this test set and then asked the machine to predict the classes of the contractile beats derived from the 'unknown' compounds group.

Example 4

Statistics

SVM accuracies of strips exposed to a drug condition were compared to those of the non-cardioactive benchmark by using Student's t-test (desired a value of 0.05) with a Bonferroni correction (m, number of tests or hypotheses, was dependent on the number of drug additions in a screen). If the adjusted p-value was statistically significant, the drug condition was considered to have incited irregular behavior in hvCTSs and was labeled as cardioactive. The Bonferroni correction was also applied when examining changes in specific parameters.

To analyze the performance of the multi-class models, confusion matrices were generated for each of the 50 runs. In a confusion matrix, M, the precision and recall rates were defined as the following:

$$Precision_i = \frac{M_{ii}}{\sum_{j=1}^{n} M_{ij}}$$

$$Recall_j = \frac{M_{ii}}{\sum_{i=1}^{n} M_{ij}}$$

The precision and recall rates were calculated for each of the classifiers. To further summarize these metrics, the $F_1$ score, harmonic mean of precision and recall, was computed and defined as the following:

$$F_1 Score_i = \frac{2 \times Precision_i \times Recall_i}{Precision_i + Recall_i}$$

A model that is perfect would achieve a $F_1$ score of 1. If a model were composed of s-number of classes and had random classifiers, the expected $F_1$ score would be $$\frac{1}{s}.$$

To assess the model as a whole, accuracy, defined as:

$$Accuracy_{model} = \frac{\sum_{i=1}^{n} M_{ii}}{\sum_{i=1}^{n} \sum_{j=1}^{n} M_{ij}}$$

was calculated. In summarizing the 50 runs of each model, all calculated metrics were averaged and a confusion matrix containing the average number of contractile events over all runs was provided. All reported sample sizes (n) refer to independent tissue strips (biological replicates). All descriptive statistics are in the format of mean±standard deviation.

Example 5

Class Relationship Metrics

The concentration of a library compound that induced the most similar cardioactive effects as the compound of interest was determined. This class relationship metric was computed by first selecting the compound of interest at a desired concentration and performing a series of binary SVM among the tested range of a library compound. For each concentration of the library compound, the closer the SVM accuracy was to 50%, the more defined boundaries of the compounds overlapped and the more similar the cardioactive effects were. This relationship between SVM accuracy and tested concentration range was presumed to behave in a Gaussian manner with the centroid representing the concentration that would elicit the most similar effects. The Gaussian fit was set with 50% as the lower limit and the highest achieved SVM accuracy as the upper limit. If the original SVM accuracies reached the 50% mark and remained around this value for subsequent concentrations, only the first concentration to reach the 50% was included in the fit to accurately model one side of the Gaussian curve.

Example 6

Optimization of Binary and Multi-Class SVM Classifiers

To optimize the binary SVM classifiers, a non-linear kernel, radial basis function, was implemented. The hvCTS data was allocated with one third representing the test set and the remainder serving as the training set. We maintained a balanced number between the vehicle-treated strips and those exposed to a cardioactive compound of the model (n=6, 7, 8, 9, or 10). Since the number of vehicle strips (n=28) always outweighed those treated with drugs, we randomly selected a subset of the vehicle-treated tissue strips that equaled the sample size for each SVM run. We tuned both the box constraint and sigma parameter of each run with a geometric progression approach. To prevent overfitting, we performed a 5-fold cross validation. It should be noted that if more than half of the tissue strips become unresponsive to the electrical stimulation at a given concentration, the SVM accuracy for that condition was automatically designated as 100% and binary SVM was not performed. A total of 50 SVM runs were performed for each concentration to account for the variation and random selection of data sets.

For the multi-class models, a criterion of 85% binary SVM accuracy was used to determine the specific concentration of a compound that would be included in the library. This criterion was chosen as it was as a reference point where the cardioactive effects of a compound would be prominent, but can still define generalizable boundaries from those of other compounds. The value of 85% was specifically chosen as it was approximately the midpoint between the maximum achievable separation (100%) and a minimum bound that would ensure cardioactivity. We defined the minimum bound as the largest sum of mean SVM accuracy and one standard deviation across all vehicle studies, resulting in a bound of 69.34% (mean SVM accuracy of 53.45% and standard deviation of 15.89%). The criterion of at least 6 responsive tissue strips was to ensure that within the test sets there were data from at least two strips for all runs.

For the creation and optimization of the multi-class models, a one-vs.-one strategy with binary SVM learners was used. An error-correcting output codes approach was used to summarize results and classify. Binary learners were again tuned in regards to the box constraint and sigma parameter. A 10-fold cross validation was performed on the entire model. Similarly, this multi-class classification and prediction process was repeated a total of 50 times.

REFERENCES

Chen, A., Lee, E., Tu, R., Santiago, K., Grosberg, A., Fowlkes, C., and Khine, M. (2014). Integrated platform for functional monitoring of biomimetic heart sheets derived from human pluripotent stem cells. Biomaterials 35, 675-683.

Dempsey, G. T., Chaudhary, K. W., Atwater, N., Nguyen, C., Brown, B. S., Mcneish, J. D., Cohen, A. E., and Kralj, J. M. (2016). Cardiotoxicity screening with simultaneous optogenetic pacing, voltage imaging and calcium imaging. J. Pharmacol. Toxicol. Methods 81, 240-250.

Dick, E., Rajamohan, D., Ronksley, J., and Denning, C. (2010). Evaluating the utility of cardiomyocytes from human pluripotent stem cells for drug screening. Biochem. Soc. Trans. 38, 1037-1045.

Dietterich, T. G. (1995). Solving Multiclass Learning Problems via Error-Correcting Output Codes. J. Artif. Intell. Res. 263-286.

Eng, G., Lee, B. W., Protas, L., Gagliardi, M., Brown, K., Kass, R. S., Keller, G., Robinson, R. B., and Vunjak-novakovic, G. (2016). Autonomous beating rate adaptation in human stem cell-derived cardiomyocytes. Nat. Commun. 7, 1-10.

FDA (2005). Guidance for Industry: S7B Nonclinical Evaluation of by Human Pharmaceuticals Guidance for Industry.

Ferriman, A. (2000). UK licence for cisapride suspended Cancer drug may cause heart failure. Br. Med. J. 321, 2000.

Guo, L., Qian, J., Abrams, R., Tang, H., Weiser, T., Sanders, M. J., and Kolaja, K. L. (2011). The Electrophysiological Effects of Cardiac Glycosides in Cardiomyocytes and in Guinea Pig Isolated Hearts. Cell. Physiol. Biochem. 27, 453-462.

Guo, L., Coyle, L., Abrams, R. M. C., Kemper, R., Chiao, E. T., and Kolaja, K. L. (2013). Refining the Human iPSC-Cardiomyocyte Arrhythmic Risk Assessment Model. 136, 581-594.

Harmer, A. R., Abi-Gerges, N., Morton, M. J., Pullen, G. F., Valentin, J. P., and Pollard, C. E. (2012). Validation of an in vitro contractility assay using canine ventricular myocytes. Toxicol. Appl. Pharmacol. 260, 162-172.

Harris, G., and Koli, E. (2005). Lucrative Drug, Danger Signals and the F.D.A. New York Times 1-9.

Harris, K., Aylott, M., Cui, Y., Louttit, J. B., McMahon, N. C., and Sridhar, A. (2013). Comparison of electrophysiological data from human-induced pluripotent stem cell-derived cardiomyocytes to functional preclinical safety assays. Toxicol. Sci. 134, 412-426.

Huebsch, N., Loskill, P., Deveshwar, N., Spencer, C. I., Judge, L. M., Mandegar, M. A., Fox, C. B., Mohamed, T. M. A., Ma, Z., Mathur, A., et al. (2016). Miniaturized iPS-Cell-Derived Cardiac Muscles for Physiologically Relevant Drug Response Analyses. Sci. Reports 6, 1-12.

Katz, A., Lifshitz, Y., Bab-Dinitz, E., Kapri-Pardes, E., Goldshleger, R., Tal, D. M., and Karlish, S. J. D. (2010). Selectivity of digitalis glycosides for isoforms of human Na,K-ATPase. J. Biol. Chem. 285, 19582-19592.

Lee, E. K., Kurokawa, Y. K., Tu, R., George, S. C., and Khine, M. (2015). Machine learning plus optical flow: a simple and sensitive method to detect cardioactive drugs. Sci. Rep. 5.

Li, X., Zhang, R., Zhao, B., Lossin, C., and Cao, Z. (2016). Cardiotoxicity screening: a review of rapid-throughput in vitro approaches. Arch. Toxicol. 90, 1803-1816.

Liu, J., Lieu, D. K., Siu, C. W., Fu, J. D., Tse, H. F., and Li, R. A. (2009). Facilitated maturation of Ca 2+ handling properties of human embryonic stem cell-derived cardiomyocytes by calsequestrin expression. Am J Physiol Cell Physiol 297, 152-159.

Lu, H. R., Whittaker, R., Price, J. H., Vega, R., Pfeiffer, E. R., Cerignoli, F., Towart, R., and Gallacher, D. J. (2015). High throughput measurement of Ca++ dynamics in human stem cell-derived cardiomyocytes by kinetic image cytometry: A cardiac risk assessment characterization using a large panel of cardioactive and inactive compounds. Toxicol. Sci. 148, 503-516.

Luna, J. I., Ciriza, J., Garcia-ojeda, M. E., Kong, M., Herren, A., Lieu, D. K., Li, R. A., Fowlkes, C. C., Khine, M., and McCloskey, K. E. (2011). Multiscale Biomimetic Topography for the Alignment of Neonatal and Embryonic Stem Cell-Derived Heart Cells. Tissue Eng. Part C 17.

Lundy, S. D., Zhu, W.-Z., Regnier, M., and Laflamme, M. A. (2013). Structural and Functional Maturation of Cardiomyocytes Derived from Human Pluripotent Stem Cells. Stem Cells Dev. 22, 1991-2002.

Maddah, M., Heidmann, J. D., Mandegar, M. a, Walker, C. D., Bolouki, S., Conklin, B. R., and Loewke, K. E. (2015). A Non-invasive Platform for Functional Characterization of Stem-Cell-Derived Cardiomyocytes with Applications in Cardiotoxicity Testing. Stem Cell Reports 4, 621-631.

Martin, R. L., Lee, J., Cribbs, L. L., Perez-reyes, E., and Hanck, D. A. (2000). Mibefradil Block of Cloned T-Type Calcium Channels 1. J. Pharmacol. Exp. Ther. 295, 302-308.

Millard, D. C., Strock, C. J., Carlson, C. B., Aoyama, N., Juhasz, K., Goetze, T. A., Stoelzle-Feix, S., Becker, N., Fertig, N., January, C. T., et al. (2016). Identification of Drug-Drug Interactions In Vitro: A Case Study Evaluating the Effects of Sofosbuvir and Amiodarone on hiPSC-Derived Cardiomyocytes. Toxicol. Sci. 154, 1-9.

Navarrete, E. G., Liang, P., Lan, F., Sanchez-Freire, V., Simmons, C., Gong, T., Sharma, a., Burridge, P. W., Patlolla, B., Lee, a. S., et al. (2013). Screening Drug-Induced Arrhythmia Events Using Human Induced Pluripotent Stem Cell-Derived Cardiomyocytes and Low-Impedance Microelectrode Arrays. Circulation 128, S3-S13.

Pillekamp, F., Haustein, M., Khalil, M., Emmelheinz, M., Nazzal, R., Adelmann, R., Nguemo, F., Rubenchyk, O., Pfannkuche, K., Matzkies, M., et al. (2012). Contractile Properties of Early Human Embryonic Beta-Adrenergic Stimulation Induces Positive Chronotropy and Lusitropy but Not Inotropy. Stem Cells Dev. 21, 2111-2121.

Pointon, A., Pilling, J., Dorval, T., Wang, Y., Archer, C., and Pollard, C. (2016). High-Throughput Imaging of Cardiac Microtissues for the Assessment of Cardiac Contraction during Drug Discovery. Toxicol. Sci. kfw227.

Ravenscroft, S. M., Pointon, A., Williams, A. W., Cross, M. J., and Sidaway, J. E. (2016). Cardiac Non-myocyte Cells Show Enhanced Pharmacological Function Suggestive of Contractile Maturity in Stem Cell Derived Cardiomyocyte Microtissues. Toxicol. Sci. 152, 99-112.

Scott, C. W., Zhang, X., Abi-Gerges, N., Lamore, S. D., Abassi, Y. A., and Peters, M. F. (2014). An impedance-based cellular assay using human iPSC-derived cardiomyocytes to quantify modulators of cardiac contractility. Toxicol. Sci. 142, 331-338.

Serrao, G. W., Turnbull, I. C., Ancukiewicz, D., Kim, D. E., Kao, E., Cashman, T. J., Hadri, L., Hajjar, R. J., and Costa, K. D. (2012). Myocyte-depleted engineered cardiac tissues support therapeutic potential of mesenchymal stem cells. Tissue Eng. Part A 18, 1322-1333.

Shum, A. M. Y., Che, H., Wong, A. O., Zhang, C., Wu, H., Chan, C. W. Y., Costa, K., Khine, M., Kong, C., and Li, R. A. (2017). A Micropatterned Human Pluripotent Stem Cell-Based Ventricular Cardiac Anisotropic Sheet for Visualizing Drug-induced Arrhythmogenicity. Adv. Mater. 29.

Sirenko, O., Crittenden, C., Callamaras, N., Hesley, J., Chen, Y.-W., Funes, C., Rusyn, I., Anson, B., and Cromwell, E. F. (2013). Multiparameter in vitro assessment of compound effects on cardiomyocyte physiology using iPSC cells. J. Biomol. Screen. 18, 39-53.

Steinberg, S. F. (1999). The Molecular Basis for Distinct B-Adrenergic Receptor Subtype Actions in Cardiomyocytes. Circ. Res. 85, 1101-1111.

Turnbull, I. C., Karakikes, I., Serrao, G. W., Backeris, P., Lee, J., Xie, C., Senyei, G., Gordon, R. E., Li, R. A., Akar, F. G., et al. (2014). Advancing functional engineered cardiac tissues toward a preclinical model of human myocardium. Fed. Am. Soc. Exp. Biol. 28, 644-654.

US Food and Drug Administration (2007). FDA Announces Discontinued Marketing of GI Drug, Zelnorm, for Safety Reasons. 10-11.

Wang, J., Chen, A., Lieu, D. K., Karakikes, I., Chen, G., Keung, W., Chan, C. W., Hajjar, R. J., Costa, K. D., Khine, M., et al. (2013). Biomaterials Effect of engineered anisotropy on the susceptibility of human pluripotent stem cell-derived ventricular cardiomyocytes to arrhythmias. Biomaterials 34, 8878-8886.

Weng, Z., Kong, C.-W., Ren, L., Karakikes, I., Geng, L., He, J., Chow, M. Z. Y., Mok, C. F., Chan, H. Y. S., Webb, S. E., et al. (2014). A Simple, Cost-Effective but Highly Efficient System for Deriving Ventricular Cardiomyocytes from Human Pluripotent Stem Cells. Stem Cells Dev. 23, 1704-1716.

Williams, G. H. (1988). Converting-enzyme inhibitors in the treatment of hypertension. N. Engl. J. Med. 319, 1517-1525.

Wong, B. S., Manabe, N., and Camilleri, M. (2010). Role of prucalopride, a serotonin (5-HT4) receptor agonist, for the treatment of chronic constipation. Clin. Exp. Gastroenterol. 3, 49-56.

Yang, X., Pabon, L., and Murry, C. E. (2014). Engineering Adolescence: Maturation of Human Pluripotent Stem Cell-Derived Cardiomyocytes. Circ. Res. 114, 549-561.

Zhang, D., Shardin, I., Lam, J., Xian, H.-Q., Snodgrass, R., and Bursac, N. (2014). Tissue-engineered cardiac patch for advanced functional maturation of human ESC-derived cardiomyocytes. Biomaterials 34, 5813-5820.

Ziupa, D., Beck, J., Franke, G., Feliz, S. P., Hartmann, M., Koren, G., Zehender, M., Bode, C., Brunner, M., and Odening, K. E. (2014). Pronounced Effects of HERG-Blockers E-4031 and Erythromycin on APD, Spatial APD Dispersion and Triangulation in Transgenic Long-QT Type 1 Rabbits. PLoS One 9.

What is claimed is:

1. A platform configured to detect cardioactivity of a drug candidate compound, the platform comprising:
   (a) a living cell or a tissue that is capable of exerting a force in response to exposure to the drug candidate compound;
   (b) a detector that measures onset, duration and magnitude of the force as a function of time by the living cell or tissue upon exposure to the drug candidate compound;
   (c) a memory configured to store data related to the onset, duration and magnitude of the force detected by the detector; and
   (d) one or more processing unit(s) configured to:
      (i) employ machine learning, wherein a supervised learning algorithm uses a training set to teach one or more model(s) of cardioactivity, allowing the model(s) to learn over time to perform automated drug classification on novel data sets,
      (ii) process the data related to the onset, duration and magnitude of the force as a function of time of the living cell or tissue upon exposure to the drug candidate compound,
      (iii) consolidate a plurality of parameters pertaining to the onset, duration and magnitude of the force as a function of time into one or more index/indices of cardioactivity, and
      (iv) compare the one or more index/indices of cardioactivity to known indices of cardioactivity to determine if the drug candidate compound is capable of modulating cardioactivity,
   wherein the platform is configured to apply a plurality of electrical pacing frequencies to the living cell or tissue and wherein cellular response data elicited by the applied plurality of electrical pacing frequencies is captured and analyzed.

2. The platform according to claim 1, wherein the living cell or tissue is a model of cardiac muscle fiber.

3. The platform according to claim 1, wherein the living cell or tissue is configured as a human cardiac tissue strips (hCTS).

4. The platform according to claim 1, wherein the machine learning utilizes predetermined parameters of onset, duration and magnitude of the force as a function of time to classify the response by the living cell or tissue to the drug.

5. The platform according to claim 4, wherein the predetermined parameters of the onset, duration and magnitude of the force as a function of time comprise one or more of the following parameters:
   (a) a prescribed pacing frequency;
   (b) a captured pacing frequency;
   (c) a maximum force generated (amplitude);
   (d) a duration of rise from a cutoff level to maximum force in a contraction phase;
   (e) a duration of decline from maximum force to a cutoff level in a relaxation phase;

(f) an area under the curve of rise from a cutoff level to maximum force;
(g) an area under the curve of decline from maximum force to a cutoff level;
(h) a maximum change of force as a function of time ($\Delta F/\Delta t$) of contraction phase; and
(i) a maximum change of force as a function of time ($\Delta F/\Delta t$) of relaxation phase.

6. The platform according to claim 5, wherein:
(d) the duration of the rise from the cutoff level to maximum force in the contraction phase is from 95% cutoff to max force (contraction phase),
(e) the duration of the decline from maximum force to the cutoff level in the relaxation phase is from max force to 95% cutoff (relaxation phase),
(f) the area under the curve of the rise from the cutoff level to maximum force is from 95% cutoff to max force,
(g) the area under the curve of the decline from maximum force to a cutoff level is from max force to 95% cutoff,
or wherein the predetermined parameters of the onset, duration and magnitude of the force as a function of time may further comprise one or more of the following parameters:
(j) a duration of rise from 50% cutoff to max force,
(k) a duration of decline from max force to 50% cutoff,
(l) an area under the curve of rise from 50% cutoff to max force,
(m) an area under the curve of decline from max force to 50% cutoff,
(n) a duration of rise from 25% cutoff to max force,
(o) a duration of decline from max force to 25% cutoff to max force,
(p) an area under the curve of rise from 50% cutoff to max force, and
(q) an area under the curve of decline from max force to 50% cutoff.

7. The platform according to claim 1, wherein the measurement of onset, duration and magnitude of the force as a function of time comprises a measure of cell or tissue motion and/or electrical conduction and/or calcium flux and wherein the detector is capable of detecting motion and/or electrical conduction and/or calcium flux in the living cell or tissue following exposure to the drug.

8. The platform according to claim 7, wherein the electrical conduction detected corresponds to one or more of a micro-impedance signal and an electrophysiological signal.

9. The platform according to claim 1, wherein the processing unit is configured to output dosing information of the drug candidate compound to modulate cardioactivity based upon a comparison to cardioactivity data from one or more known compound(s).

10. The platform according to claim 1, further comprising a library of drug types and/or families and corresponding measures of cardioactivity of the library of drug types and/or families stored in the memory.

11. The platform according to claim 10, wherein each drug type or drug family is characterized by a plurality of distinct compounds within the drug type or drug family.

12. A method of screening a drug to determine cardioactivity of the drug using the platform according to claim 1, the method, comprising:
(a) exposing a test cell or a tissue to the drug,
(b) applying a plurality of electrical pacing frequencies to the test cell or the tissue and wherein cellular response data elicited by the applied plurality of electrical pacing frequencies is captured and analyzed,
(c) quantifying data relating to onset, duration and magnitude of a force as a function of time measured from the test cell in response to the drug,
(d) comparing the data measured from the test cell or the tissue to corresponding data relating to onset, duration and magnitude of the force as a function of time in a library of known drug types, and
(e) determining cardioactivity of the drug.

13. The method of claim 12, wherein the data measured from the test cell is indicative of cardiotoxicity.

14. The method of claim 12 wherein the test cell or tissue is a human cardiac tissue construct.

15. The method according to claim 12, wherein a degree to which a compound is cardiotoxic/cardioactive is determined.

16. The method according to claim 12, wherein machine learning is used to form predetermined parameters of the onset, duration and magnitude of the force as a function of time indicative of cardioactivity of known drug types.

17. The method according to claim 12, wherein said comparing the data relating to onset, duration and magnitude of the force as a function of time of the test cell to corresponding data of known drug types is done by a series of binary classifications.

18. The method according to claim 12 comprising calculating a singular quantitative index generated by a supervised learning algorithm to consolidate a plurality of parameters of data relating to onset, duration and magnitude of the force as a function of time into a singular quantitative index.

19. The method of claim 12, wherein the drug candidate is determined to be a $Ca^{2+}$ channel blocker; an adrenergic agonist; a cardiac glycoside; an hERG $K^+$ channel blocker; an ACE inhibitor or a non-cardioactive, nonsteroidal ant-inflammatory drug.

* * * * *